US006829955B1

(12) United States Patent
Mahgerefteh

(10) Patent No.: US 6,829,955 B1
(45) Date of Patent: Dec. 14, 2004

(54) PARTICLE SIZE DISTRIBUTION ANALYSER

(75) Inventor: Haroun Mahgerefteh, Finchley (GB)

(73) Assignee: Technometrics Ltd., Finchley (GB)

( * ) Notice: Subject to any disclaimer, the term of this patent is extended or adjusted under 35 U.S.C. 154(b) by 0 days.

(21) Appl. No.: 10/148,279

(22) PCT Filed: Nov. 23, 2000

(86) PCT No.: PCT/GB00/04458
§ 371 (c)(1),
(2), (4) Date: Dec. 10, 2002

(87) PCT Pub. No.: WO01/38851
PCT Pub. Date: May 31, 2001

(30) Foreign Application Priority Data

Nov. 25, 1999 (GB) .............................................. 9927899

(51) Int. Cl.$^7$ ............................................ G01N 27/00
(52) U.S. Cl. ..................................................... 73/865.5
(58) Field of Search ............................... 73/865.5, 865, 73/32 A

(56) References Cited

U.S. PATENT DOCUMENTS

| 5,222,605 A | | 6/1993 | Pogue ........................ 209/239 |
| 6,072,308 A | * | 6/2000 | Mahgerefteh et al. ..... 324/71.1 |

FOREIGN PATENT DOCUMENTS

| GB | 2 231 154 | 7/1990 |
| GB | 2 237 381 | 1/1991 |
| GB | 2 294 772 | 8/1996 |
| WO | WO 90/09573 | 8/1990 |

* cited by examiner

*Primary Examiner*—Robert Raevis
(74) *Attorney, Agent, or Firm*—Cohen, Pontani, Lieberman & Pavane

(57) ABSTRACT

There is described a particle size distribution analysis apparatus comprising an oscillatory assembly, the oscillatory assembly comprising a receptacle for receiving a powder sample and having an opening through which powder may be discharged, the opening being variable in size, and support means allowing the receptacle to reciprocate along an arcuate path, entry means for introducing the sample into the receptacle, adjusting means for varying the size of the opening, bias means to urge the oscillatory assembly towards a datum position, and drive means to induce oscillations of the oscillatory assembly. Detector means may be provided to determine a characteristic of the oscillations of the oscillatory assembly and hence determine the mass of powder remaining in the receptacle. Alternatively, the oscillatory assembly of the apparatus may be allowed to come to a rest position between episodes of oscillation, and the angular orientation of the rest position may be measured to determine the mass of powder remaining. Also described are methods for operation of the particle size analysis apparatus.

56 Claims, 22 Drawing Sheets

PARTICLE SIZE DISTRIBUTION ANALYSER

This application is a U.S. National Phase Application under 35 USC 371 of International Application PCT/GB00/04458 filed 23 Nov. 2000 (published in English).

BACKGROUND OF THE INVENTION

This invention relates to an apparatus and methods for determining particle size distribution of powders, and in particular but not exclusively, to apparatus able to automatically determine the proportion of different particle sizes within a test sample.

Heretofore, many devices of high sensitivity have been developed for particle size measurement. These either rely on direct dimensional measurement and operate by sieving and/or microscopy, or depend on detecting a physical response, i.e. electrozone, various light beam interference techniques or sedimentation. Most of these techniques are either time consuming, require expensive equipment or are capable of analysing small samples only. In addition, the majority are not suitable for online monitoring. This is an important drawback since in the manufacture, for example, of industrial powders as diverse as paint pigments, cement and photocopier toner, there is a requirement to control tightly the particle size distribution during production. An online capability, where size distribution is measured in real time during the manufacturing process, allows immediate readjustment of the process parameters to control the particle size of the material produced.

It is known from GB 2294772 to provide apparatus to address some of these problems by fluidising a powder within a vibrating helical coiled spring and extending this coiled spring so that progressively larger particles are able to leave through the gap between adjacent turns of the coiled spring. A disadvantage of such apparatus is that it cannot readily measure the mass of powder within the coiled spring as this mass is small compared to the total vibrating mass of the coiled spring and ancillary structure.

DESCRIPTION OF RELATED ART

According to one aspect of the present invention there is disclosed a particle size analysis apparatus comprising: an oscillatory assembly comprising (a) a receptacle for receiving a powder sample entry means for introducing a particle into the receptacle; an opening in the receptacle which may be adjusted in size, adjuster means for adjusting the size of the opening support means allowing the vessel to reciprocate along an arcuate path, bias means to urge the oscillatory assembly towards a datum position; and drive means to induce oscillations of the oscillatory assembly.

It is preferred in such an apparatus that the receptacle is a helical coiled spring defining a lumen for containing the power sample and that most of the mass of the oscillatory assembly is arranged to result in a relatively low moment of inertia of the oscillatory assembly about the axis whilst the coiled spring is mounted at a distance from the axis so that powder within it has a relatively high moment of inertia about the axis. In one embodiment, determination of the change in total moment of inertia of the oscillatory system caused by particles escaping from the coiled spring allows the mass of powder remaining within the coiled spring to be determined.

In an alternative embodiment, mass of the power sample remaining in the receptacle of spring is measured by detecting a rest position of the oscillatory assembly when the drive means is inoperative.

In yet another embodiment, the powder exiting the receptacle may be collected and weighed.

The coiled spring is preferably coil-bound in its unstressed state, so as to be able to retain small particles. However, the overriding requirement is that the gap between adjacent turns of the coiled spring is smaller than the smallest particles of interest. The resolution of the apparatus may be further improved by supporting the coiled spring so as to limit the magnitude of transverse oscillations. Excessively large transverse oscillations cause a periodic additional separation of the coils of the coiled spring which introduces uncertainty as to the effective size of the gap between adjacent turns of the coiled spring. However, some flexing of the coiled spring is desirable to prevent particles from adhering to the coiled spring; the movement produced between adjacent turns by flexing of the coiled spring helps to loosen adhering particles.

The powder to be tested may be introduced into the coiled spring via a funnel inlet. Captive particles such as ballotini spheres may be used within the coiled spring to aid vibro-dispersion of the powder along the coiled spring and to reduce agglomeration of the powder under test within the coiled spring.

A stepper motor may be used advantageously to extend the coiled spring in conjunction with a threaded shaft and a captive nut which is prevented from rotating but is able to move axially of the shaft. One end of the coiled spring may be fixed in relation to the axial direction of the shaft, and the other end fixed relative to the nut, so that rotation of the shaft moves the nut axially of the shaft and thus extends or contracts the coiled spring.

The restoring means is preferably a steel leaf spring although alternatives are possible including a torsion spring, a spring that is coiled or suitable magnetic devices to emulate the action of a spring, i.e. to apply a restoring force proportional to displacement from a datum position. Where a leaf spring is used it is preferably tapered towards the pivot axis.

The pivot axis is preferably horizontal in use and parallel to the longitudinal axis of the spring, although deviations from this orientation are possible. The bearings for the pivot axis are preferably ball bearings, but alternatively may be any suitable low-friction bearing such as "cup and cone" or other type. Air bearings are also suitable provided transverse float is not excessive, and the use of torsion springs also as bearings allows the integration of the pivotal axis and restoring means. Cup and cone bearings are preferably provided with an axial pre-load by a biasing means by, for example, a coiled compression spring.

The drive means is advantageously provided by an electromagnet or by an electrodynamic actuator. The drive means will typically directly actuate the support although other embodiments are also possible, for example, the drive means could be coupled to the support via a resilient coupling. This latter arrangement would allow a resonator to be driven by a weakly coupled exciter.

In dynamic mass measurement techniques, a detector means detects a characteristic of the oscillating movement, and may be arranged to determine the resonant frequency of the oscillatory movement of either the support structure or the spring. This may be achieved, for example, with an infrared proximity detector or alternatively a capacitive proximity detector or a rotary shaft encoder on the pivotal axis. As an alternative, the detector means could be arranged to detect the amplitude of the oscillations or the phase difference between the drive pulses and the oscillation of the oscillatory assembly.

In a static mass measurement technique, the oscillatory assembly may be allowed to come to a rest position, and the angular orientation of the rest position may be compared to a datum position to derive the mass of the powder sample. Sensitivity may be improved by disconnecting the biasing means and using a resilient element of lower spring constant to oppose the movement of the weight of the powder about the pivot axis.

The particles that leave the spring may be collected into a suitable container. An alternative embodiment would allow particles of different size ranges to be collected into different containers for subsequent analysis, for example, by a microscope and weighing scales.

BRIEF DESCRIPTION OF THE DRAWINGS

Preferred embodiments of the present invention will now be described by way of example only and with reference to the accompanying drawings, in which.

DETAILED DESCRIPTION OF THE DRAWINGS

Figure 1:
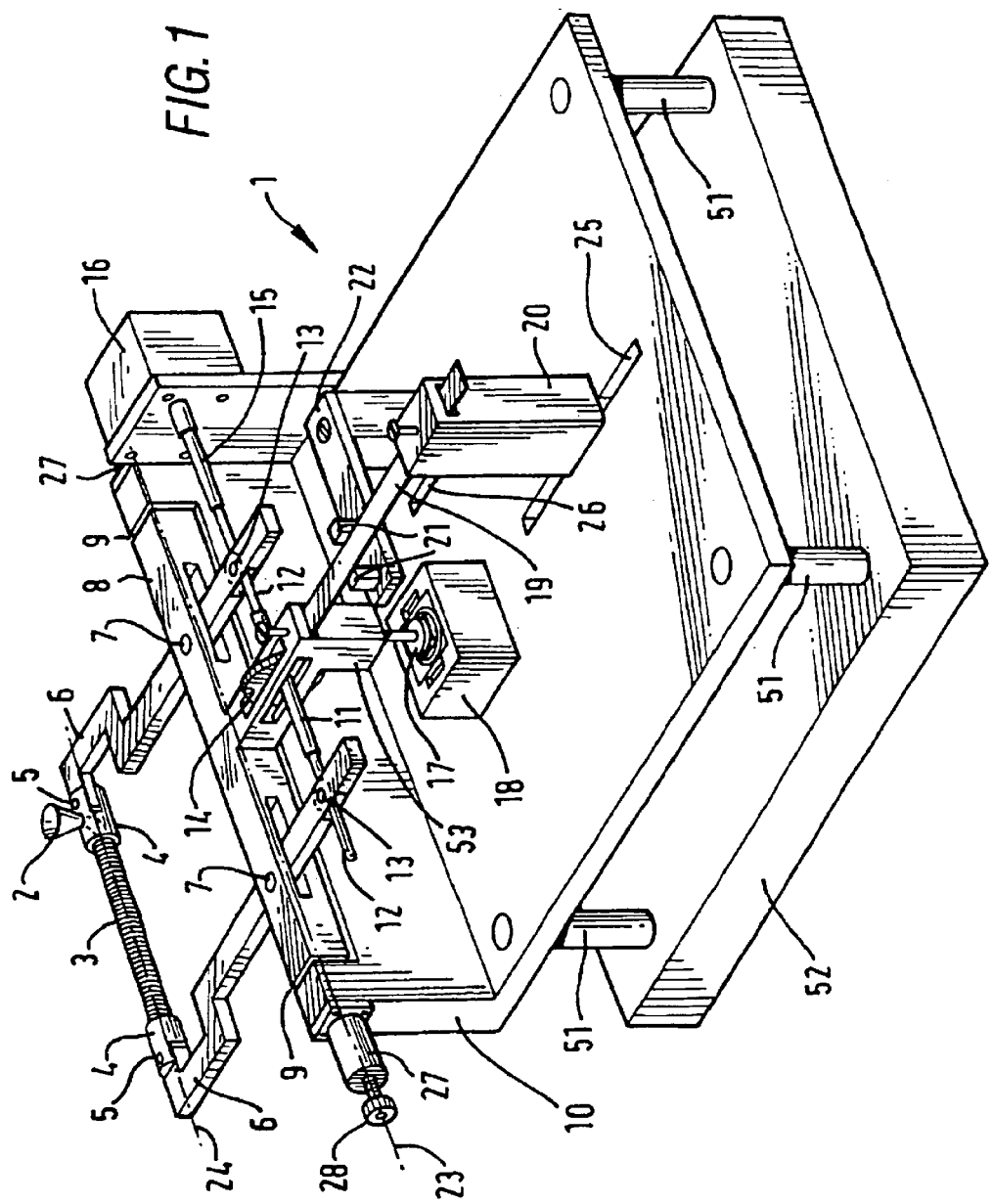
FIG. 1 is a schematic isometric view of a particle size analysis apparatus in accordance with the present invention.

FIG. 1 shows a particle size analyser 1, according to a first embodiment, comprising an inlet funnel 2 which allows powder to be introduced into an analyser spring 3 via a bore in one of two analyser spring holders 4. Each of the two analyser spring holders 4 is connected to an extender arm 6 via an analyser spring pivot 5. The two extender arms 6 connect with a T-piece 8 via a respective extender arm pivot 7. For example, the analyser spring 3 may be a helical coil-bound spring that is 10 cm long, 1 cm in diameter and made from 1.5 mm high-carbon steel wire. The analyser spring axis 24 is parallel to the pivotal axis 23.

At each end of the T-piece 8 there is provided a cup and cone bearing 9 which pivotally mounts the T-piece 8 to a support frame 10 about a pivot axis 23 defined by the two cup and cone bearings 9. The cup and cone bearings 9 allow the T-piece 8 to rotate freely about the pivotal axis 23 but restrain the T-piece 8 from transverse movement, axial misalignment and endfloat. The cones (not shown) are mounted on the T-piece 8 and the cups are slidably mounted inside the support frame 10 so that they may slide along the pivot axis 23.

Each of the cup and cone bearings 9 is axially pre-loaded by a biasing means so that the bearing pre-load remains substantially constant despite thermal expansion of the components, due to ambient temperature variations. As shown in FIG. 1, each biasing means comprises a pre-load adjuster screw 28, a spring housing 27 attached to the support frame 10 and a coiled compression spring (not shown) mounted axially on the pivot axis 23 within the spring housing 27. The pre-load adjuster screws 28 may be rotated relative to their respective spring housings 27 in order to vary the degree of compression of the compression springs and hence to vary the force with which the compression springs bear upon their respective cup and cone bearings 9.

An advantage of interposing compression springs between the pre-load adjuster screws 28 and the cup and cone bearings 9 is that thermal expansion of the particle size analyser 1 will have substantially no effect on the pre-load of the cone and cup bearings 9. Otherwise, the pre-load and hence the friction of the cup and cone bearings 9 may vary with temperature which would vary the natural resonant frequency of the oscillatory assembly.

Extension of the analyser spring 3 is effected by rotation of an extender shaft 11 which has two oppositely threaded sections 12. Each threaded section 12 bears upon an extender arm 6 via an extender shaft pivot 13. An extender shaft wheel 14 is provided for manual rotation of the extender shaft 11 although rotation of the extender shaft 11 will more typically be achieved by a stepper motor 16. A flexible coupling 15 is provided to allow the stepper motor 16 to rotate the extender shaft 11 without interfering in the motion of the T-piece 8. Alternatively motor 16 may be mounted on the T-piece to oscillate therewith. Extension of the analyser spring 3 may, for example, open up the gap between adjacent turns (of the analyser spring 3) from 0–0.6 mm.

Mounted to the support frame 10 is a solenoid 18 having a movable core 17. The solenoid core 17 is fixed to the T-piece 8, at a point remote from the pivot axis 23.

The application of suitable pulses of electric current to the solenoid coil 18 causes the inward attraction of the solenoid core 17 thereby initiating, and sustaining, an oscillatory rocking motion in the T-piece 8.

The restoring means is provided by a leaf or reed spring 19 connected between a central projection 53 of the T-piece 8 and the reed spring support 20. (The extender shaft 11 is received in a clearance opening in the projection 53 to allow freedom for its movement.) The reed spring 19 is securely clamped, at one end to the central projection 53, and at the other end to the reed spring support 20. The reed spring support 20 is slidably mounted on the reed spring slide 25 and is provided with securing means (not shown) so that it may be secured in a desired position. An infrared displacement transducer 21 is mounted adjacent to the reed spring 19 on a transducer support 22. The transducer support 22 is slidably mounted on a transducer slide 26 and may be secured in a desired position by fastening means (not shown). By adjusting the position of the transducer support 22 the infrared displacement transducer 21 may be moved along the reed spring 19 to a position where a maximum deflection may be measured.

An "oscillatory assembly" may be defined as those parts, or portions of parts, which undergo oscillatory movement during particle size analysis. In this embodiment, the oscillatory assembly comprises: the analyser spring 3, any particles within the analyser spring 3 and the feed funnel 2, the extender arms 6, the T-piece 8, the reed spring 19, the solenoid core 17, the extender shaft 11, the flexible coupling 15 and the extender shaft wheel 14.

By adjusting the position of the reed spring support 20 the restoring force of the reed spring 19 may be varied so as to arrive at a suitable value for the resonant frequency of the oscillatory assembly. The resonant frequency of the oscillatory assembly may be up to 1 kHz, but is preferably from about 10–100 Hz, varying with the mass of particles within the analyser spring.

The support frame 10 is attached to a base plate 52 with couplings 51 which damp the level of vibrations in the support frame 10. Vibrations in the support frame 10 are produced by the oscillatory assembly which, when oscillating, produces reaction forces against the support frame 10. In one embodiment, the couplings 51 are lead discs and the base plate 52 is made relatively massive to provide a sink for vibrations. Alternatively, the support frame 10 may be made massive and the couplings 51 may be anti-vibration mountings; in this case a massive base plate 52 is no longer required.

The transducer support 22 is made rigid so that any remaining vibrations of the support frame 10 do not cause perturbations in the position of the infrared displacement transducer 21 as perturbations would degrade the signal produced by the infrared displacement transducer 21 which would reduce the accuracy of the particle size distribution analyser.

Figure 2:
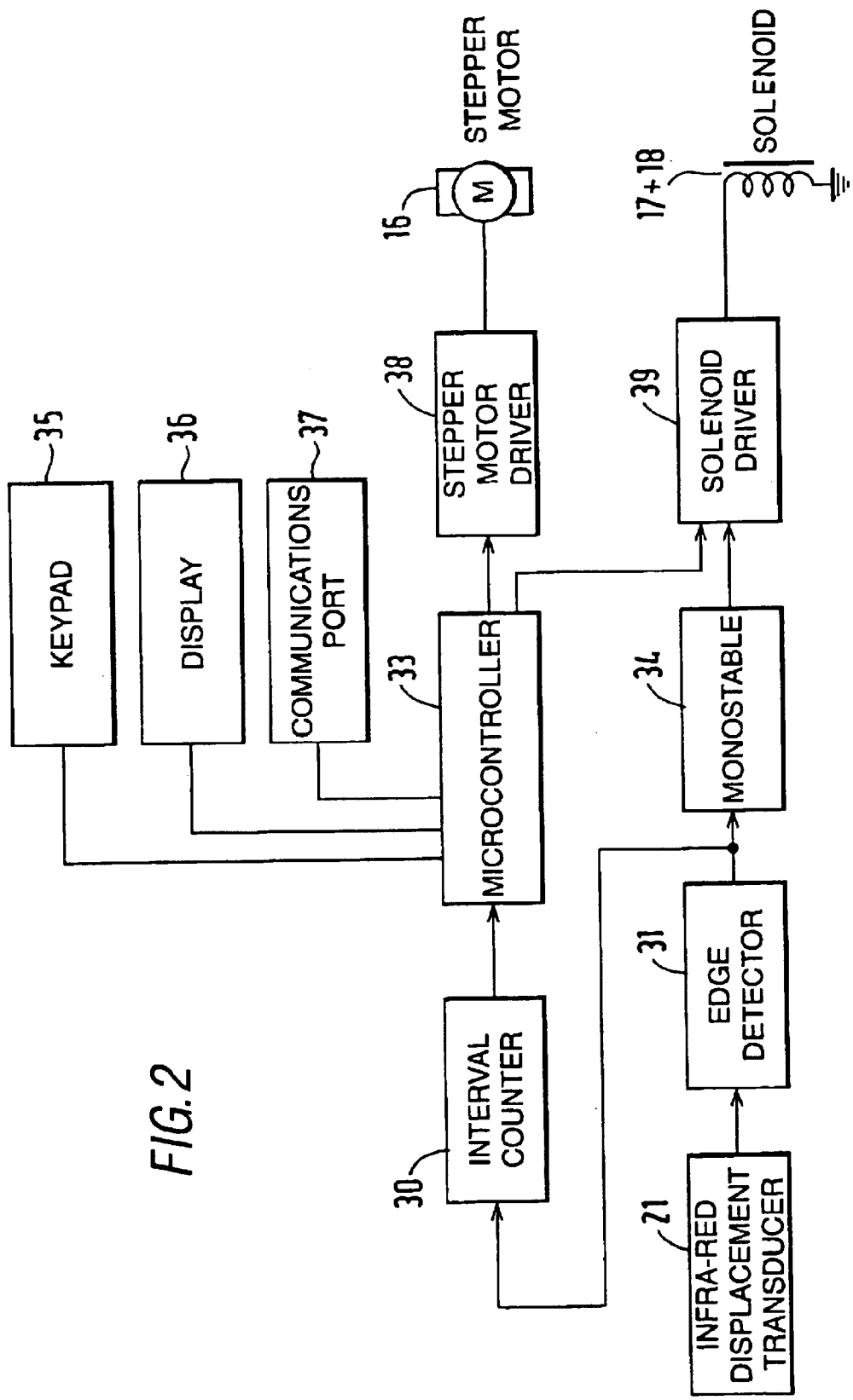
FIG. 2 is a block diagram of a system embodying the invention.

Referring to FIG. 2 the infrared displacement transducer 21 produces a signal which is routed to an edge detector 31 and from there to an interval counter 30 and to a monostable 34.

The edge detector 31 forms part of a subsystem which sustains oscillations in the T-piece 8. The edge detector 31 is used to trigger a monostable 34 at a predetermined position of the reed spring 19, and hence an angular position of the T-piece 8, that is consistent from one oscillatory cycle to the next. Preferably this position is the datum position towards which the reed spring 19 urges the T-piece 8. The edge detector 31 triggers the monostable 34 in order to produce pulses of substantially constant width so that the solenoid driver 39 may drive the solenoid with impulses of substantially constant force or alternatively constant energy.

The interval counter 30 is used to measure the period of each oscillatory cycle of the reed spring 19 and hence of the analyser spring 3. The microcontroller 33 calculates the reciprocal of the period to find the oscillatory frequency of the oscillatory assembly.

The microcontroller 33 controls a stepper motor driver 38 which operates a stepper motor 16 so as to extend and contract the analyser spring 3 via the extender shaft 11. Thus the microcontroller 33 is able to control the analyser spring 3 extension and also determine the mass of powder within the analyser spring 3 by measuring the oscillation frequency of the oscillatory assembly using the infrared displacement transducer 21 and the interval counter 30.

The microcontroller 33 also interfaces to a keypad 35, a display 36 and a communications port 37. The keypad 35 and the display 36 allow parameters and commands to be entered into the system and the results displayed, respectively. The communications port 37, for example implementing the RS232 standard, allows data and commands to be communicated with another computer.

Once started, oscillations of the oscillatory assembly will continue indefinitely by virtue of the infrared displacement transducer 21 and the solenoid 17, 19. However, to initiate oscillations it is necessary to force the solenoid driver 39 to drive the solenoid 17, 18 with a starting pulse of current. The microcontroller 33 may be arranged to force the solenoid driver 39 to emit a starting pulse whenever it is necessary to initiate oscillations of the T-piece 8. Once analysis of a test sample has finished the motion of the oscillatory assembly may be terminated by arranging for the microcontroller 33 to disable the solenoid driver 39.

Figure 3:
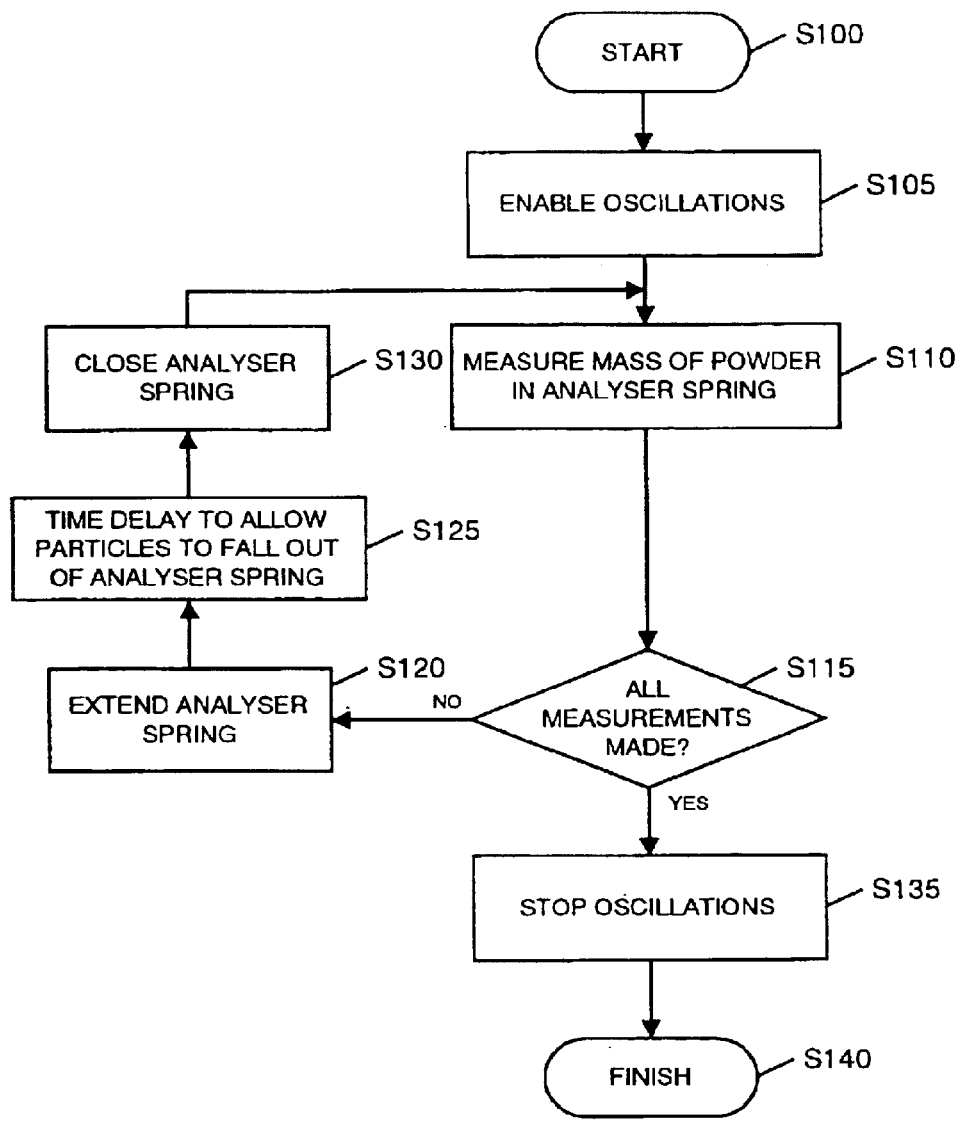
FIG. 3 is a flowchart of a measurement procedure for the particle size analyser which closes the coiled spring to perform measurements.

FIG. 3 is a flow chart which illustrates a method of operation of the particle size distribution analyser in which the analyser spring 3 is incrementally extended from the coil-bound condition to a fully extended condition, returning to the coil-bound condition to perform measurements. During this process the smallest particles of the test powder and then progressively the larger particles will fall out of the spring, through the gaps between adjacent turns of the extended analyser spring 3, reducing the mass and hence the moment of inertia of the oscillatory assembly. This change of mass will cause a change in the resonant frequency and also in the damping factor $\xi$ of the oscillatory assembly. Hence if the drive amplitude is maintained constant, both the amplitude of oscillations and the resonant frequency will vary as a function of the mass of the test powder remaining within the analyser spring 3.

Step 100 is the start of the measurement procedure and it is assumed that the analyser spring 3 is coil-bound, that the oscillatory assembly is motionless, and that a test sample has been introduced into the analyser spring 3.

At step 105 oscillations at the natural frequency of the oscillating assembly are initiated and are left to continue until terminated later on in the measurement procedure.

At step 110 the mass of the particles remaining within the analyser spring 3 is measured.

Step 115 is a test to determine whether the analysis of the test sample has been completed: for example, a given analysis may consist of ten measurements each corresponding to a different extension of the analyser spring 3. These measurements may be arbitrarily placed within the operating range of the analyser spring 3 and could, for example, all be clustered around a particle size range which is of particular interest. If further measurements are to be taken, then at step 120 the analyser spring 3 is extended so that the gap between adjacent turns corresponds to the upper limit of the next particle size range that is to be measured.

Step 125 is an interval during which the analyser spring 3 is oscillated for sufficient time for substantially all the particles which are smaller than the gap between adjacent turns to fall out of the analyser spring 3.

Step 130 contracts the analyser spring 3 to the coil-bound condition. When all measurements are completed, the process moves to step 135 and the monostable 34 and solenoid driver 39 are turned off allowing the oscillatory assembly to come to rest and at step 140 the measurement procedure terminates.

An example of the results that a test sample could produce in conjunction with a particular test is as follows:

| Analyser Spring Aperture Size, μm | Natural Frequency, Hz | Powder Mass, g |
|---|---|---|
| 0 | 27.0 | 10.0 |
| 125 | 27.3 | 7.0 |
| 300 | 27.6 | 5.0 |
| 350 | 27.7 | 4.5 |
| 400 | 27.8 | 3.7 |
| 450 | 28.0 | 2.0 |
| 700 | 28.3 | 0.0 |

In this example the natural frequency of the oscillatory assembly, without any particles within it, is 28.3 Hz. The reduction in the natural frequency (due to the mass of particles within the analyser spring) allows the mass of particles within the analyser spring to be calculated.

Figure 4:
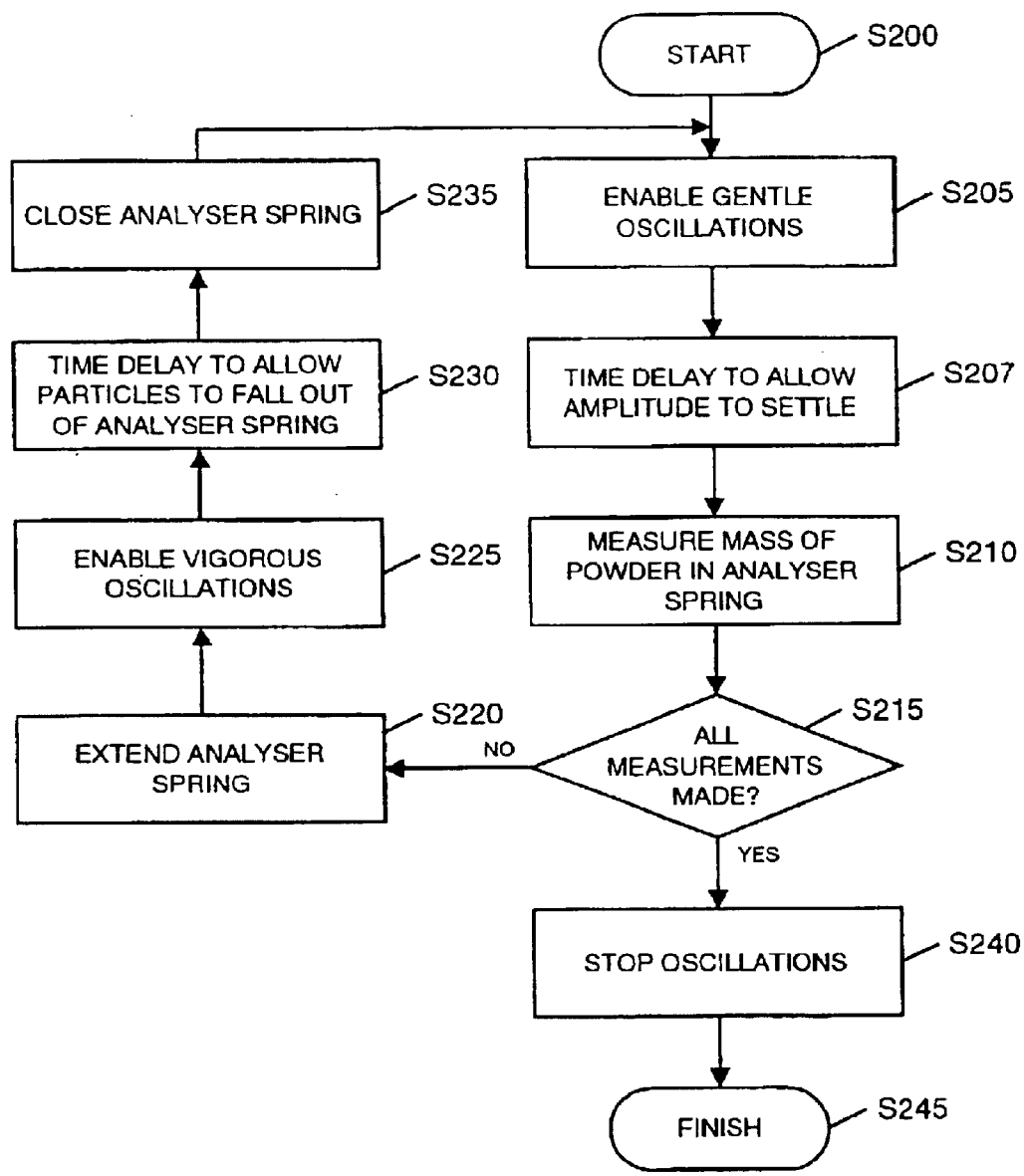
FIG. 4 is a flowchart of a second measurement procedure which uses two different oscillatory amplitudes.

FIG. 4 shows a flowchart for an improved measurement procedure which uses different amplitudes of oscillation at different parts of the measurement procedure. In the method of FIG. 3, only one oscillation amplitude for the oscillatory assembly is used which is a compromise between a sufficiently large amplitude to give satisfactory agitation and vibro-fluidisation of the particles within the analyser spring 3 and a sufficiently small amplitude to give good measurement accuracy. The vibro-fluidisation and agitation of the particles changes their effective mass within the analyser spring 3 which leads to measurement errors. These errors may be reduced by making measurements at a reduced amplitude of oscillation and therefore reduced vertical acceleration of the spring, in particular by ensuring that the peak upwards acceleration of the analyser spring 3 is less than 1 g, in order to prevent particles from becoming fluidised. The accuracy with which the mass of powder within the analyser spring 3 is determined may be further improved by reducing the peak acceleration of the analyser spring 3 still further (below 1 g) for example, to 0.1 g. The peak acceleration of the analyser spring, and hence of the oscillatory assembly, may not be reduced indefinitely because (since the amplitude is proportional to the acceleration) other effects will increasingly degrade the measurement accuracy. Examples of these other effects are friction within the mechanism and the sensitivity of the infra-red displacement transducer being insufficient to properly discern low amplitude oscillations.

Vigorous oscillations are used when the spring is extended, to agitate and vibro-fluidise the particles so that the particles may fall out of the analyser spring 3; gentle oscillations, which do not fluidise the particles, are used during the measurement of the mass of the particles within the analyser spring 3. In this example, the vigorous oscillations have a peak-to-peak amplitude of the order of 2–3 mm while the gentle oscillations are of the order of 0.1 mm. More than two different amplitudes of oscillations could also be used with this method.

Step 200 of FIG. 4 is the start of a measurement procedure and it is assumed that a test sample has been introduced into the analyser spring 3, that the analyser spring 3 is coil-bound and that the oscillatory assembly is stationary.

Step 205 initiates oscillations of the oscillatory assembly, these oscillations continue for the remainder of the measurement procedure although their amplitude is varied.

After a time delay at step 207 to allow the amplitude to settle, an accurate measurement of the mass of the particles within the analyser spring 3 is made at step 210.

At step 215 a test is made to determine whether the analysis is complete, this test corresponds to that made at step 115 of FIG. 3. If there are further measurements to be performed, step 220 is performed which extends the analyser spring 3 to the extension required for the next measurement point.

Step 225 changes a parameter of either or both the monostable 34 or the solenoid driver 39 so that vigorous oscillations result.

Step 230 is a time delay in the measurement procedure which allows substantially all of the particles which are smaller than the gap between adjacent turns of the analyser spring 3 to fall out.

Step 235 contracts the analyser spring 3 so that the coil-bound condition is regained. In this measurement procedure, the re-closing of the analyser spring 3 at step 235 is performed during vigorous oscillations although the coil-bound condition could instead be reattained during gentle oscillations. However, the method of FIG. 4 prevents particles from being trapped between adjacent turns of the analyser spring 3, as it closes, by means of agitation and vibro fluidisation during step 235.

If, at step 215, the analysis of the test sample within the analyser spring 3 is complete then oscillations are disabled at step 240 and the measurement procedure is complete at step 245.

Figure 5A:
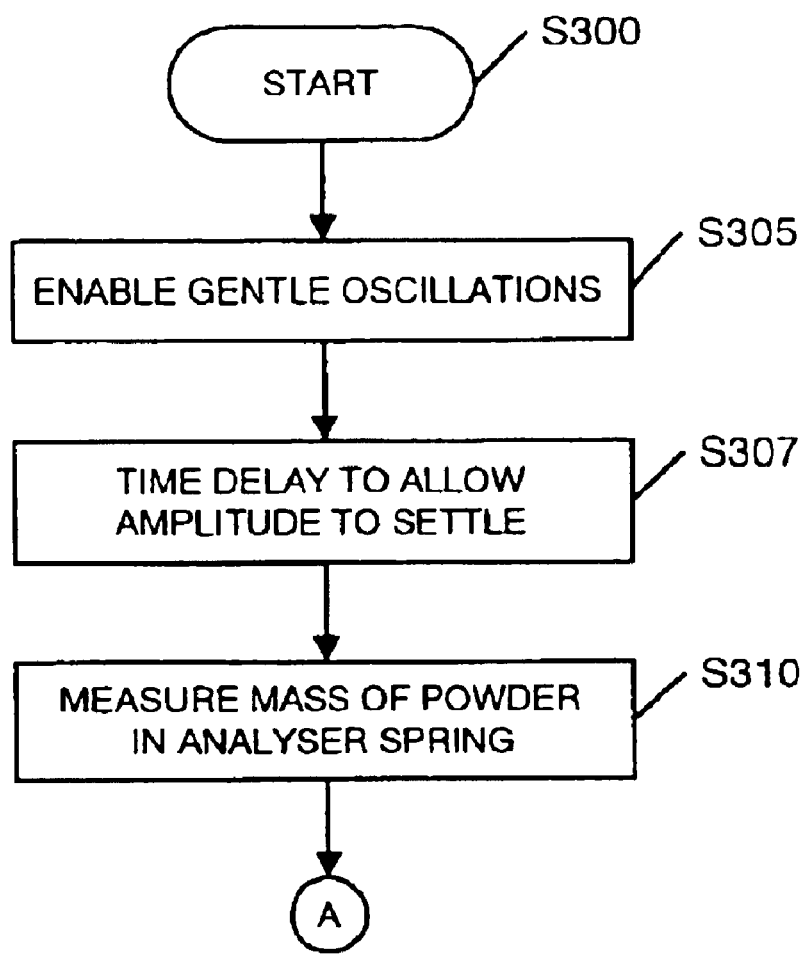
FIGS. 5a, 5b and 5c illustrate a flowchart of a third measurement procedure which keeps the coiled spring extended when measuring relatively large particles.
Figure 5B:
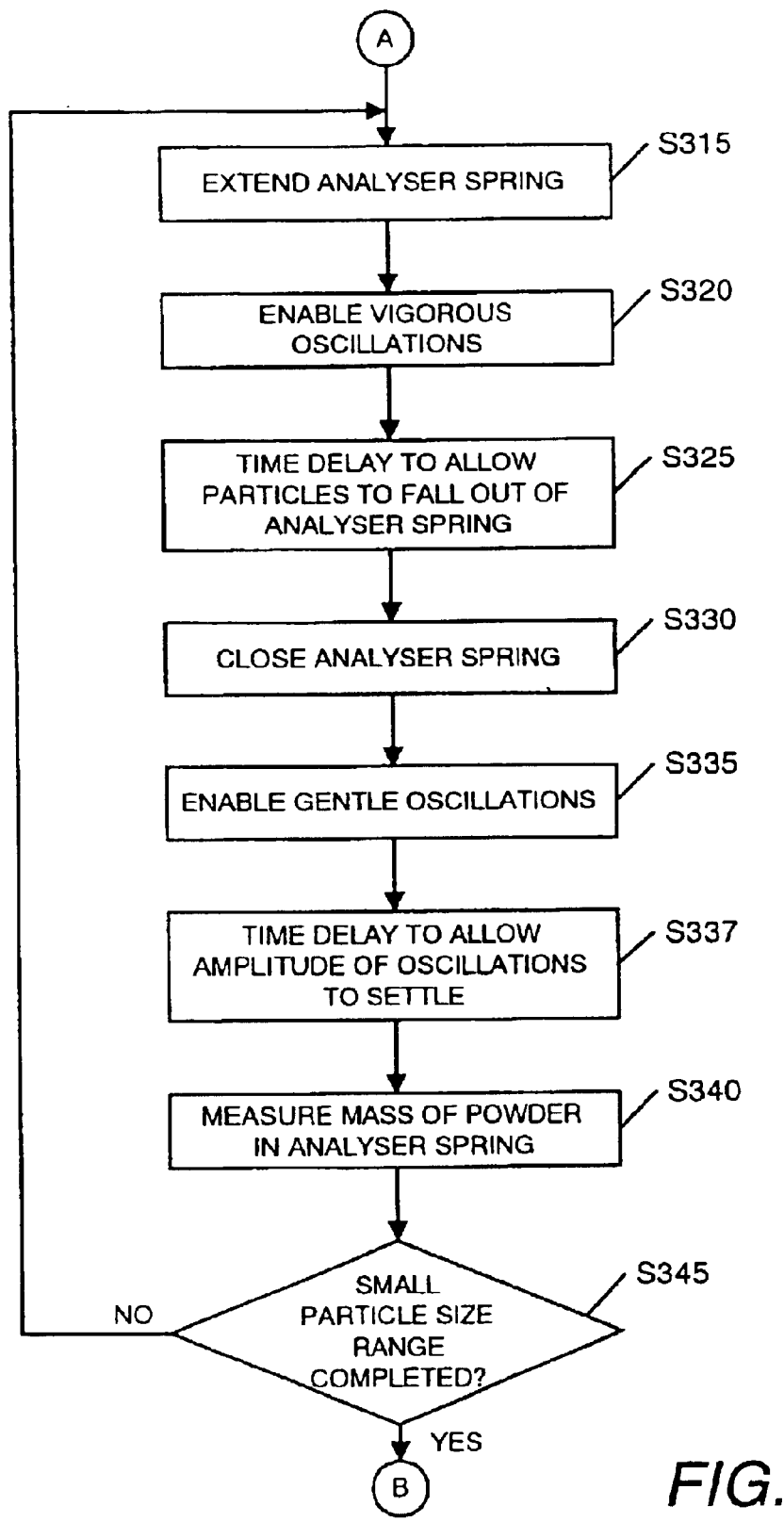
Figure 5C:
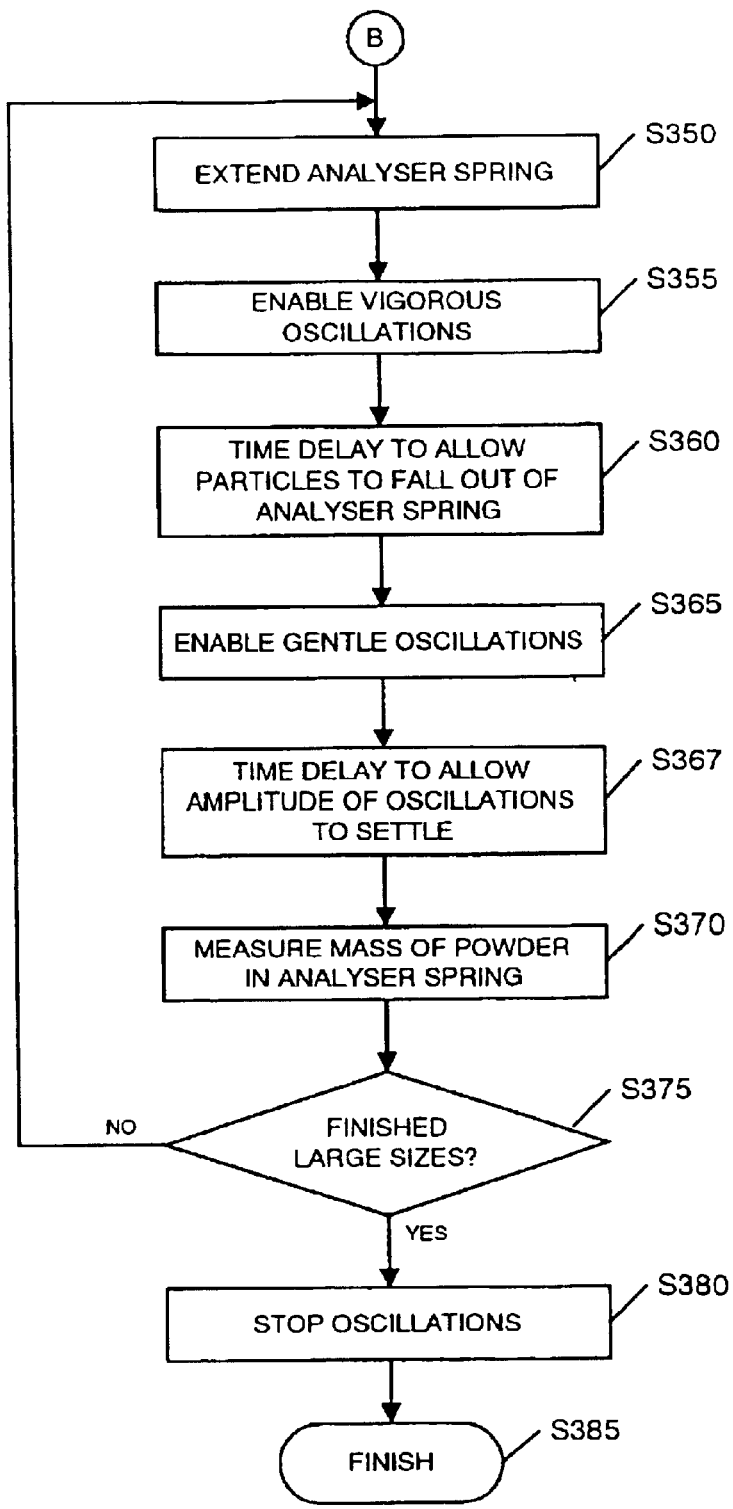

FIG. 5 shows an alternative measurement procedure which makes allowance for the fact that the characteristics of a coil-bound analyser spring change substantially during the initial extension out of the coil-bound condition. When coil-bound, the analyser spring 3 behaves substantially like a rigid tube and, as can be seen in the example of FIG. 6, this behaviour changes substantially after a small extension.

Figure 6:
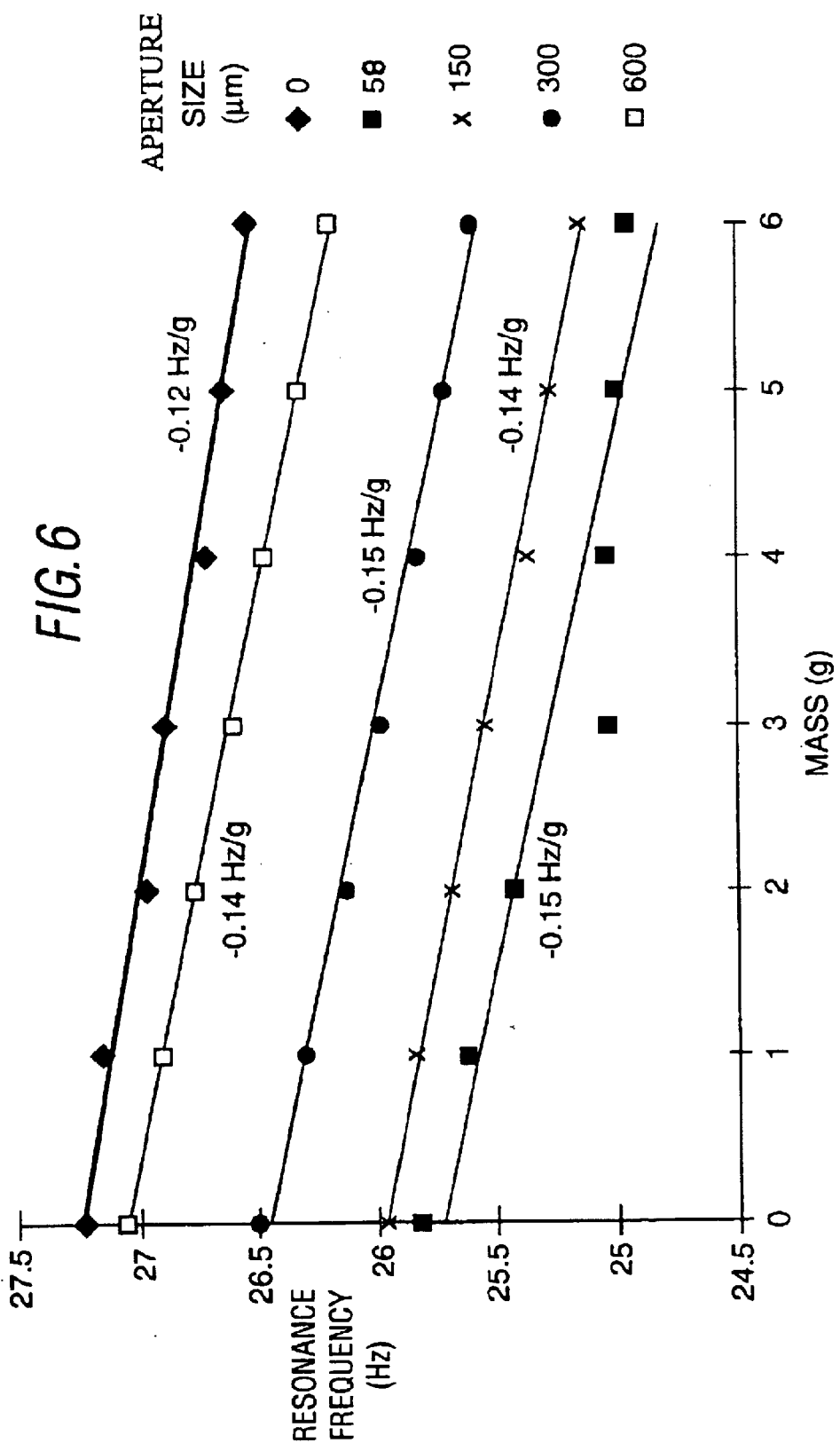
FIG. 6 is an example of the resonant frequency of the particle size distribution analyser versus the mass of particles within the coiled spring at 5 different extensions of the coiled spring.

FIG. 6 shows how after an initial extension of the analyser spring 3, there is a relatively large drop in the resonant frequency of the oscillatory assembly even though the mass within the analyser spring 3 remains unchanged. Only after further extension does the analyser spring 3 approach the resonant frequency exhibited in the coil-bound condition.

Thus in FIG. 5, for particle sizes that correspond to only a small extension of the analyser spring 3 away from the coil-bound condition, measurements are only made by returning to the coil-bound condition, whereas for particle sizes corresponding to an extension sufficiently far away from the region in which the characteristics of the analyser spring 3 change there is no need to return the analyser spring 3 to the coil-bound condition and, instead, the analyser spring 3 may remain extended for the remainder of the measurements. Step 300 is the start of this alternative measurement procedure and it is assumed that a test sample of particles to be measured is within the analyser spring 3 and that the apparatus is not oscillating.

Step 305 initiates oscillations of the oscillatory assembly which continue until the end of the measurement procedure. At this stage the oscillations are relatively gentle. After a time delay at step 307 to allow the amplitude to settle, an accurate measurement of the mass within the analyser spring 3 is made at step 310.

At step 315 the analyser spring is extended so that measurements of the mass of particles remaining at a new measurement point may be measured. Step 320 ensures that the oscillator assembly is made to undergo relatively vigorous oscillations in order to agitate and vibro fluidise the powder within the analyser spring.

Step 325 is a time delay during which any particles smaller than the gap between the adjacent turns of the analyser spring may fall out. At step 330 the analyser spring is returned to the coil-bound condition, as before, this is done during the relatively vigorous oscillations to minimise the entrapment of particles between adjacent turns of the analyser spring.

Step 335 returns the oscillator assembly to relatively gentle oscillations so that step 340 can accurately measure the mass of particles within the analyser spring. At step 345 a test is made to determine whether the measurements that are near the coil-bound condition have been completed. If so, control passes to step 350, otherwise, control returns to step 315 to perform another measurement that is near the coil-bound condition.

Step 350 extends the analyser spring and step 355 enables vigorous oscillations of the analyser spring in order to agitate and vibro fluidise the particles within. Step 360 is a time delay to allow sufficient time for substantially all of the particles that are smaller than the gap between adjacent turns of the analyser spring to fall through these gaps. At step 365 the oscillations of the analyser spring are returned to a relatively gentle amplitude which ends the vibro fluidisation of powder within the analyser spring thus allowing step 370 to perform an accurate measurement of the mass of powder remaining within the analyser spring. Step 375 performs tests to determine whether the analysis is complete, if there are further measurement points then the analyser spring is extended to the next particle size at step 350 otherwise oscillations of the analyser spring are ended up to step 380 and the measurement procedure terminates at step 385.

FIG. 7 shows an example of an adaptive measurement procedure which improves further on the measurement procedures of FIGS. 3, 4 and 5. In those examples the analyser spring was oscillated at each new extension for a predetermined amount of time to allow all of the particles that are smaller than the gap between adjacent turns of the analyser spring to fall out through these gaps. However, the time allowed may not be sufficient to discharge the required fraction of particles from within the analyser spring. This may cause a significant degradation to the accuracy of the particle size analyser as at each measurement step it is assumed that the mass measured is entirely due to particles that are larger than the gap between adjacent turns of the analyser spring and that the contribution to the measured mass from particles which are smaller than that size is zero.

Furthermore, the time may be longer than is required, for a given sample of particles within the analyser spring. As well as unnecessarily slowing down the measurement procedure, prolonged oscillation of the analyser spring at the levels used to agitate and vibro-fluidise the particles may alter the size distribution of the particles. For example, harder particles may abrade softer particles.

As an alternative to the fixed time delay in the measurement procedures described above, the iterative procedure of steps 400 to 450 may be used to replace steps 225 and 230, steps 320 and 325 and steps 355 and 360 respectively of those procedures. Step 400 sets an index to zero prior to step 405 which sets the oscillations of the analyser spring 3 and T-piece 8 to a relatively large amplitude prior to step 410 at which a brief time delay in the procedure allows particles which are smaller than the gap between adjacent turns of the analyser spring to fall out. Step 415 returns the amplitude of the oscillations to a relatively low amplitude and a mass of particles within the analyser spring is measured at step 420, this value is given the index i which at this step will have the value of zero. At step 425 the index is incremented by 1 and at step 430 the amplitude of oscillations of the oscillator assembly is increased. At step 435 there is a brief time delay in the procedure to allow particles which are smaller than the gap between adjacent turns of the analyser spring to fall through these gaps and at step 440 the amplitude of oscillations is returned to the lower level prior to measuring the mass of particles within the analyser spring at step 445, this value is indexed with i. At step 450 a test is made to determine whether all the particles that are smaller than the gap between adjacent turns of the analyser spring have fallen through these gaps or whether further agitation and vibro-fluidisation is required to remove these smaller particles from the analyser spring. One way in which this may be done is to subtract the current indexed value of the mass within the analyser spring from the previous index value and then check if this difference is less than a threshold value, $\epsilon_M$:

$$(\text{mass}_{i-1} - \text{mass}_i) < \epsilon_M$$

$\epsilon_M$ will typically be set to a value that is comparable to the repeatability of mass measurements by the particle size distribution analyser. Thus if two consecutive measurements are sufficiently close then it is deduced that all the particles that are smaller than the gap between adjacent turns of the analyser spring have been discharged and the adaptive measurement procedure is completed. If the difference is $>\epsilon_M$, then control is passed to step 455. Step 455 checks whether the index i is less than a limit, in this case, ten and if so passes control to step 425. If the index is equal to ten then the control passes to step 460 at which point an alarm signal is generated and the adaptive measurement procedure terminates analysis of the test sample within the analyser spring. Thus step 455 provides a test to determine whether the indexed mass measurements are converging to a steady value. If an excessive number of iterations is required, in this case ten, then it is assumed that there is a problem which could, for example, be that the particles within the analyser spring are abrading each other.

In the adaptive measurement procedure of FIG. 7, successive measurements of the mass of particles within the analyser spring are used to determine when agitation and vibro-fluidisation had removed substantially all the particles that are smaller than the gap between adjacent turns of the analyser spring. Instead of successive measurements, the rate of change of, for example, the amplitude of oscillations or of the resonant frequency could be used to determine when all the smaller particles had been removed. However, other methods could also be used, for example, a light source and light detector may be arranged so that only light scattered from particles falling out of the analyser spring reaches the detector. At a new extension of the analyser spring, upon agitation and vibro-fluidisation, smaller particles will initially fall out at a relatively rapid rate but this rate will reduce because, eventually, there will be no more smaller particles remaining to fall out of the analyser spring. In this case the light detector would record an initial peak of scattered light which would gradually reduce to a sufficiently low value at which point the oscillations of the oscillatory assembly would be reduced to a relatively low amplitude prior to measuring the mass of powder remaining within the analyser spring. Other techniques for detecting particles that are falling out of the analyser spring include:

i) magnetic techniques, for example, sensing the change of flux-density produced by a ferromagnetic particle falling past a pickup coil;
 ii) capacitive means, for example, detecting the change in charge produced by a particle falling between two plates of a capacitor; and
 iii) eddy current sensors which detect the transfer of energy into a conducting particle as it falls past a coil.

Figure 7A:
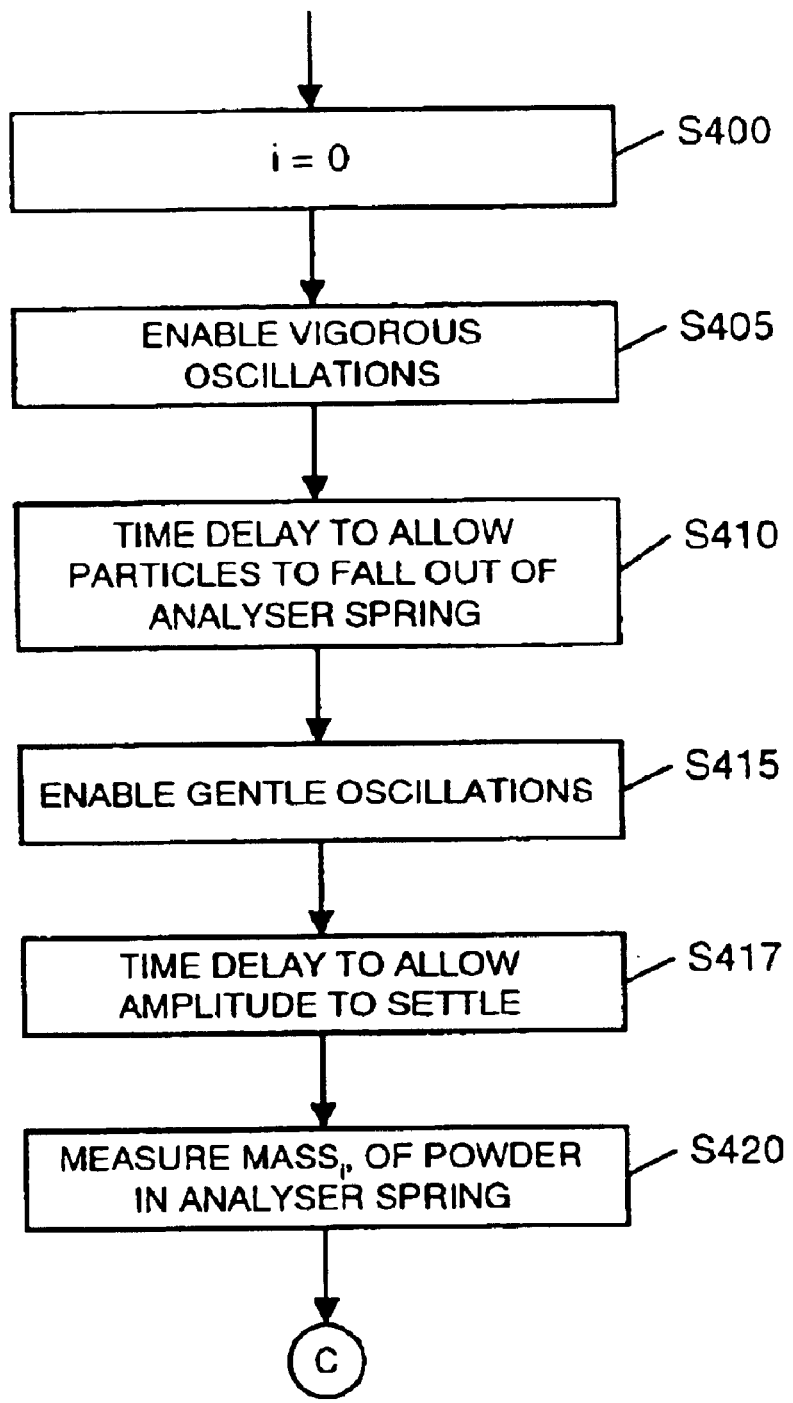
FIGS. 7a and 7b illustrate a flowchart of an adaptive measurement procedure which detects when small particles are no longer leaving the coiled spring.
Figure 7B:
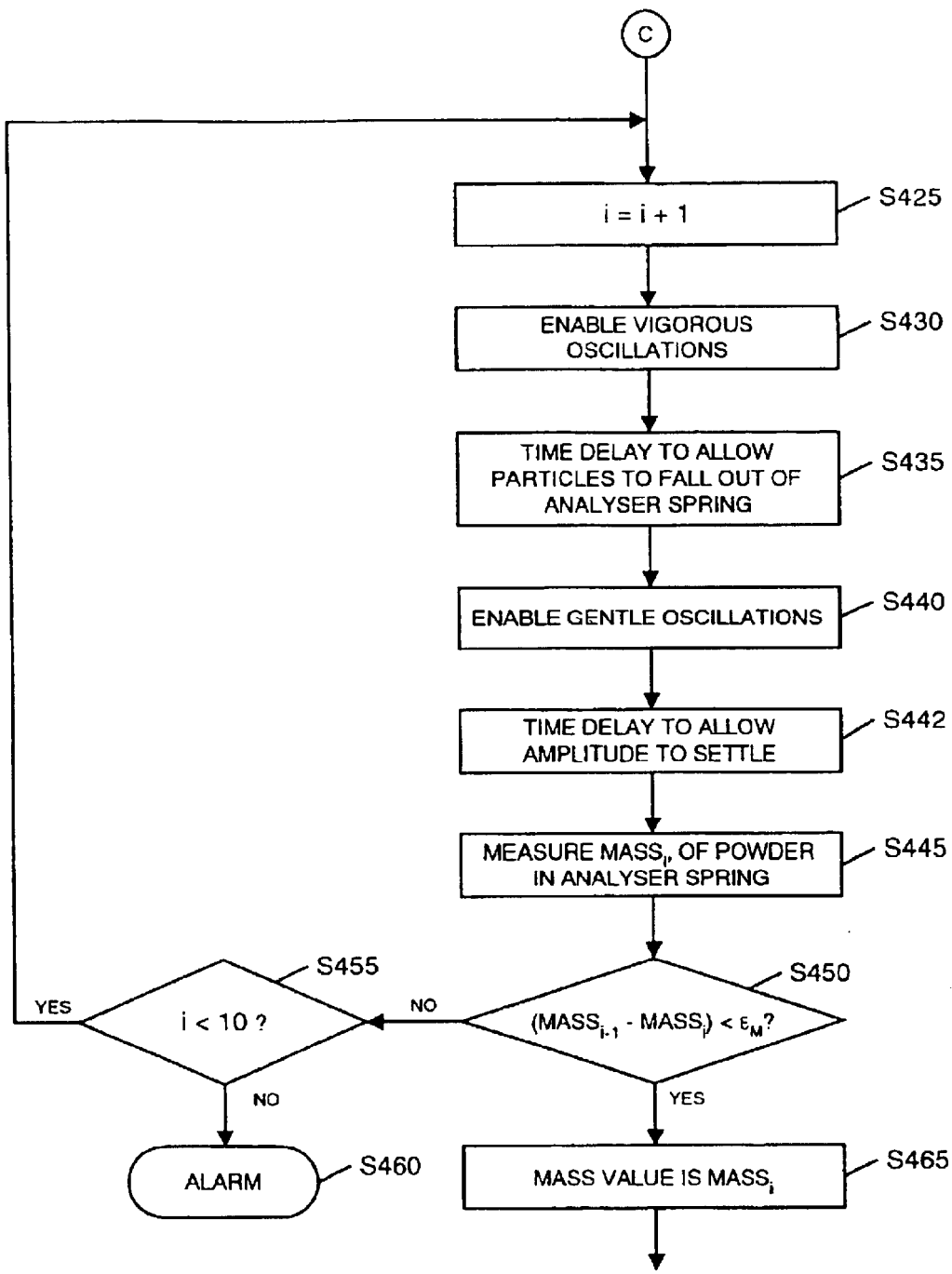
Figure 8A:
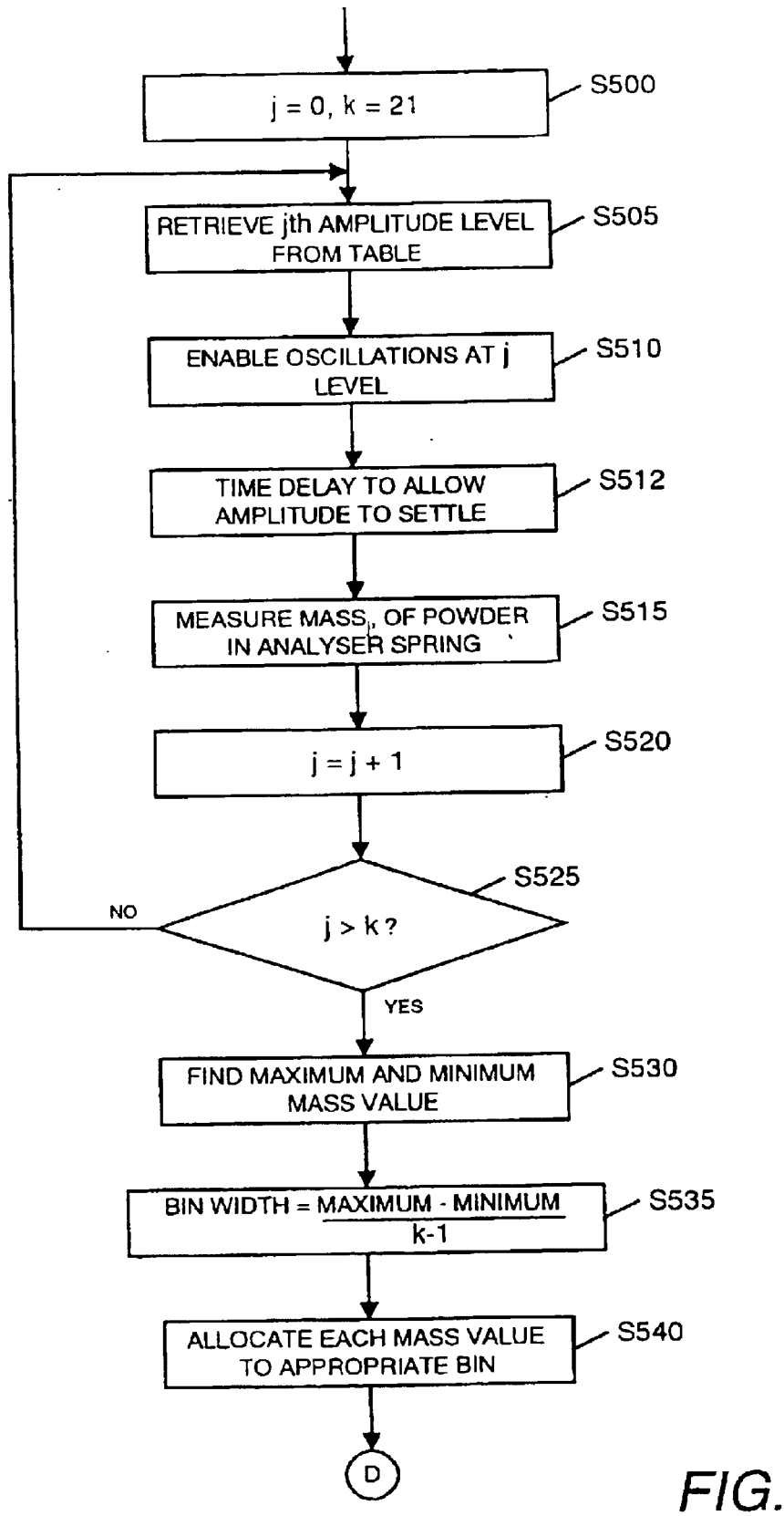
FIGS. 8a and 8b illustrate a flowchart of a measurement method which combines measurements taken at different oscillatory amplitudes.
Figure 8B:
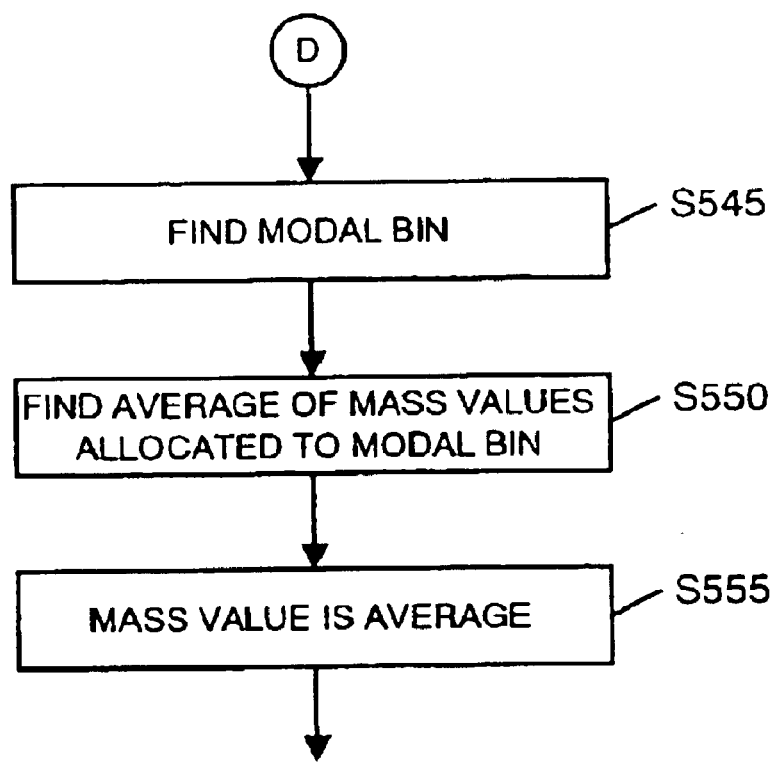

FIG. 8 shows a measurement procedure which uses a combination of measurements, at different amplitudes of oscillations of the analyser spring 3 and the T-piece 8, to produce a composite value that is less influenced by extraneous effects than the measurement values produced by, for example, the procedures of FIGS. 4, 5 and 7. Examples of extraneous effects include, but are not limited to, the change in the effective mass of the particles within the analyser spring due to vibro-fluidisation and also variations of the friction of the cup-and-cone bearings 9 with the amplitude of oscillations of the analyser spring 3 and the T-piece 8. The procedure of FIG. 8 could be used to replace steps 205 and 210 of FIG. 4; steps 335, 340, 365, 370 of FIG. 5 and/or steps 415, 420, 440, 445 of FIG. 7, respectively.

As an alternative to measuring oscillation amplitude, the oscillatory assembly may be driven by an arrangement which produces oscillation at a resonant frequency, and the resonant frequence may be measured to provide an indication of the amount of powder in the spring.

Figure 9:
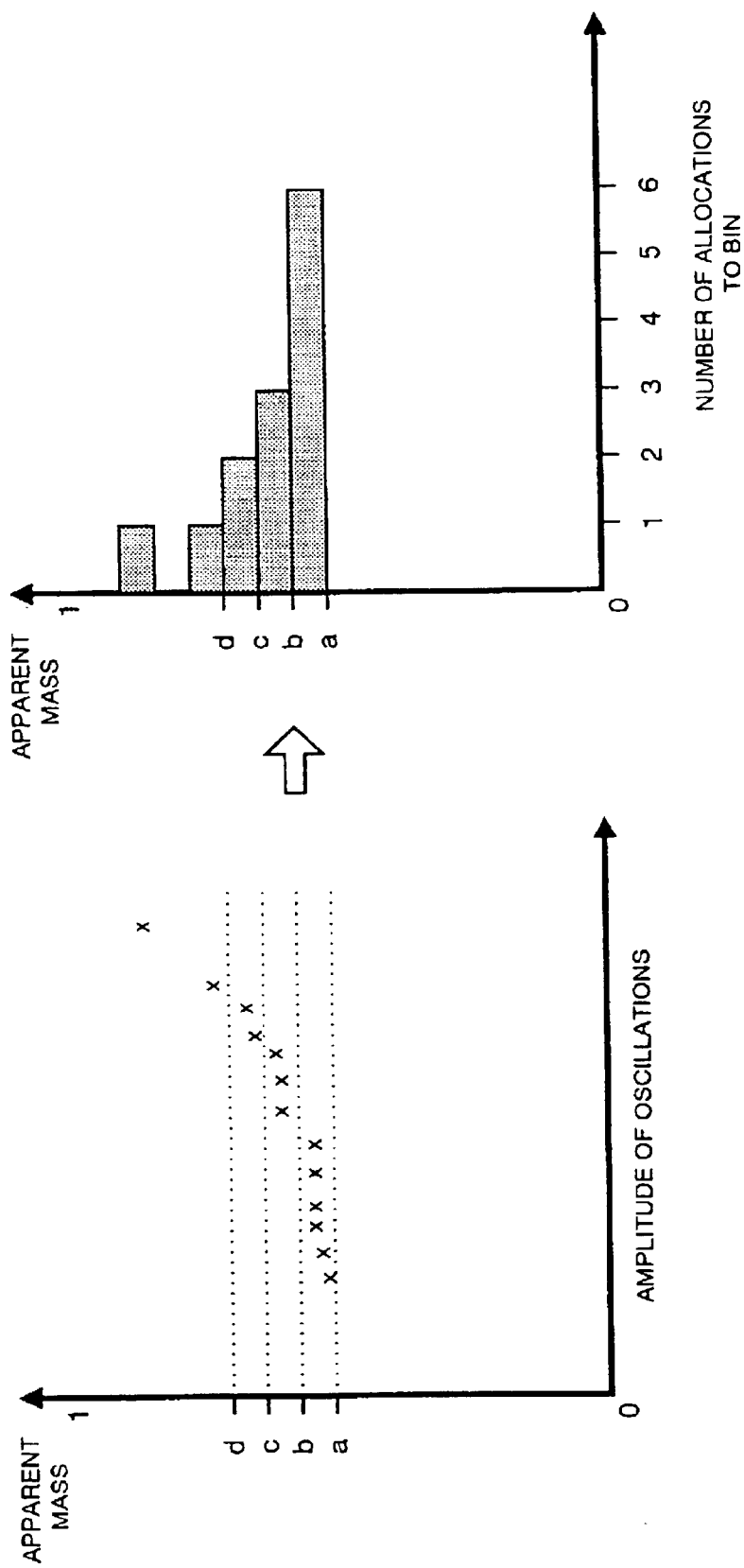
FIG. 9 is an example of the processing performed by the measurement procedure of FIG. 8.

FIG. 9 shows a bar chart which illustrates how the measurement procedure of FIG. 8 arrives at the composite value. In effect, the procedure of FIG. 8 measures the mass of particles within the analyser spring while sweeping across a variety of amplitudes of oscillation and then creates a bar-chart, FIG. 9, from which the largest bar is selected as containing the most representative measurements of the mass of particles within the analyser spring. Step 500 of FIG. 8 sets an index, j, to zero. Step 505 retrieves the jth value from a table which is used to set the amplitude of oscillations of the analyser spring 3 and the T-piece 8. Different tables could be arranged to have, for example, either a linear or a geometric progression between amplitudes. Step 510 sets the amplitude of oscillations to the jth level prior to step 515 which measures the mass of particles within the analyser spring and indexes the measured value with j. Step 520 increments j by 1 and step 525 checks whether all k (in this case, 21) of the iterations have been completed. If there are iterations outstanding (with oscillatory amplitudes for which a measurement has not yet been made) then control passes to step 505, otherwise control passes to 530. The range over which the k measurements extend is found at step 530 by selecting the highest, $mass_{maximum}$, and the lowest, $mass_{minimum}$, measurement of mass from the k values. Step 535 segments the range into k-1 bins, each bin of width $(mass_{maximum} - mass_{minimum})/k-1$. Step 540 allocates each of the k mass values to whichever bin spans the range within which that mass measurement lies. Step S45 selects the modal bin, i.e. that with which the greatest number of the k mass measurements have been associated. Step 550 determines the mean of the mass values associated with a modal bin. Step 555 is the end of this measurement procedure and returns the mean value.

An alternative procedure could be arranged to monitor, for example, the resonant frequency of the oscillatory assembly whilst decreasing the amplitude of oscillations. The cessation of vibro-fluidisation of the particles could be determined by detecting when the rate of change of resonant frequency with amplitude became zero, or in any case, became less than a threshold value $\epsilon_D$. This would indicate that vibro-fluidisation had ceased and that an accurate measurement of the mass of particles within the analyser spring could be made.

Figure 10:
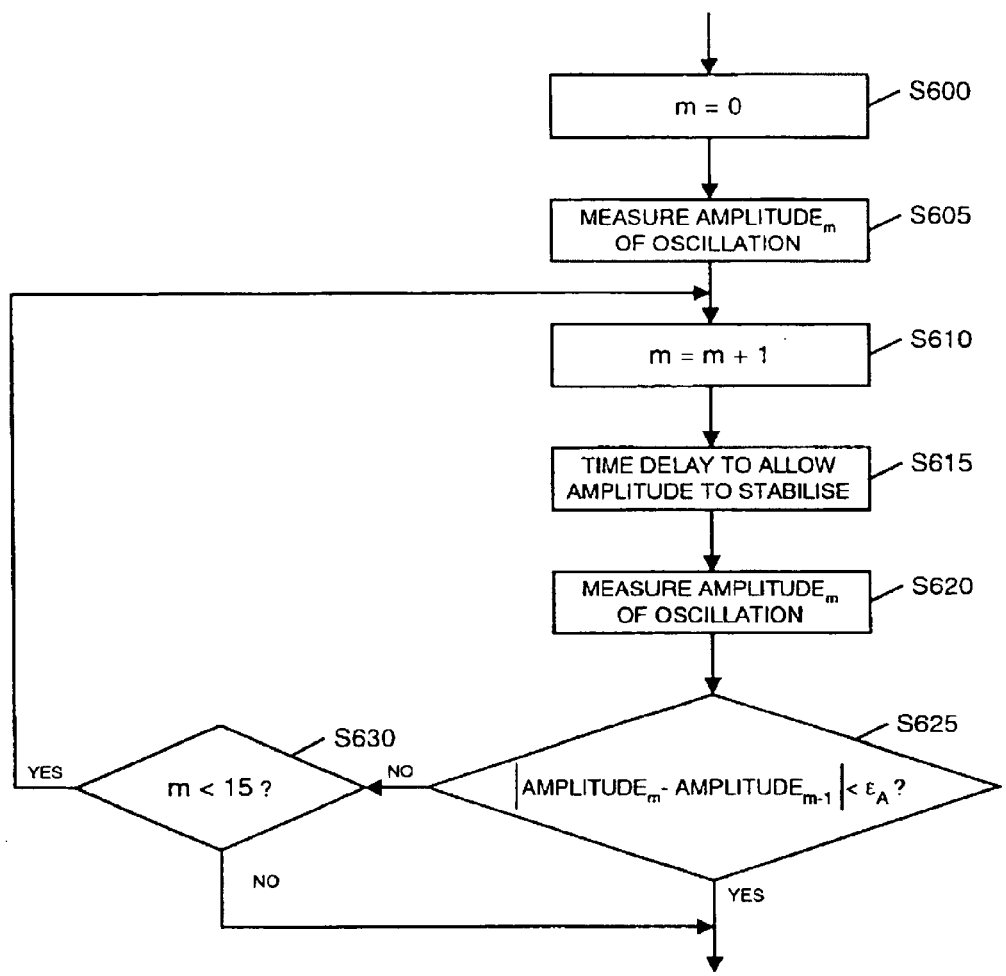
FIG. 10 is a flowchart of a measurement procedure for detecting when the amplitude of oscillations has stabilised.

FIG. 10 shows a measurement procedure that may be used in conjunction with the measurement procedures of FIGS. 4, 5, 7 and 8. In those procedures, there are time delays (at steps: S207; S307, S337, S367; S417, S442; S512 respectively) to allow the oscillation amplitude of the oscillatory assembly to settle at the gentle level prior to the measurement of the mass of particles within the analyser spring 3. This is because, as a resonant tuned system, the oscillatory assembly has a characteristic Q-factor which determines the rate at which the amplitude of unsustained oscillations diminishes. For example, a lightly damped system has a sharper resonance peak and a higher Q-factor, and so will take longer to decay to a lower amplitude than a more highly damped system. A disadvantage of allowing a fixed period of time for the oscillations to settle from the vigorous to the gentle amplitude is that that time may be too short, thereby reducing the accuracy with which the mass of particles within the analyser spring 3 is determined, or too long, thereby unnecessarily increasing the overall measurement time. The procedure of FIG. 10 uses, subject to an upper limit, as many shorter time delays as are required for the amplitude of oscillations to settle and checks after each of these shorter time delays whether the amplitude has become sufficiently stable for an accurate mass measurement. The upper limit on the number of iterations prevents the procedure from iterating indefinitely when the amplitude of oscillations is unstable as may occur, for example, when the particles are fluidised with an effective mass that is not repeatable from cycle to cycle of the oscillations. The following steps may be amalgamated and replaced by the procedure of FIG. 10: steps 105, 107, 110 of FIG. 3; steps 205, 207, 210 of FIG. 4; steps 305, 307, 310 and 335, 337, 340 and 365, 367, 370 of FIG. 5; steps 415, 417, 420 and 440, 442, 445 of FIG. 7; and steps 510, 512, 515 of FIG. 8. Step 600 initialises an index, M, to zero. At step 605 a measurement is made of the amplitude of oscillations of the oscillator assembly and this amplitude value is given the index M. The value of M is incremented by 1 as step 610 and as step 615 there is a brief pause before, at step 620, the amplitude of oscillations is measured and given the index M. At step 625 a test is made to determine whether the absolute value of $(amplitude_m - amplitude_{m-1}) < \epsilon_A$. If so, then the procedure is finished, otherwise control is passed to step 630. Step 630 checks whether a number of iterations has exceeded a limit, in this case, 15. If so, then the procedure is finished, otherwise control passes to step 610 for another iteration.

Figure 11:
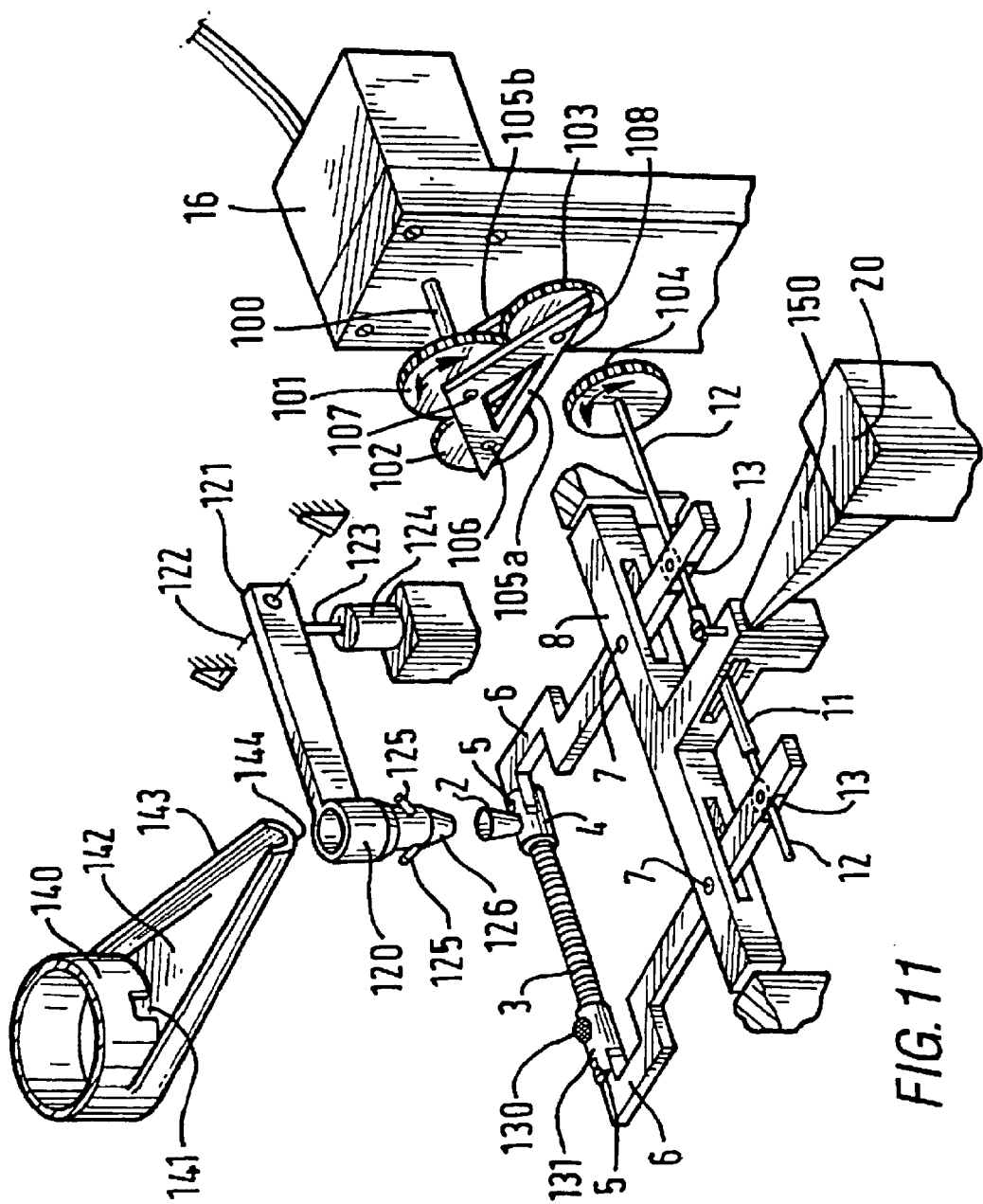
FIG. 11 is a diagram of an apparatus to which features have been added and modified so as to arrive at a second embodiment of the invention.

The apparatus as shown in FIG. 1 illustrated some of the basic features of a particle size analyser 1 according to the present invention. However, FIG. 11 shows modifications and enhancements that may be made to the apparatus of FIG.

1 in order to arrive at a second embodiment of the invention. The modifications fall into four categories:

i) a disengagable drive means comprising a stepper motor shaft 100, a primary gear 101, a first intermediate gear 102, a second intermediate gear 103, a secondary gear 104, an idler frame 105a, b, a first idler shaft 106, a frame mount 107 and a second idler shaft 108;

ii) a sample loading means comprising a funnel support arm 121, a funnel support arm axis 122, a support arm solenoid core 123, a support arm solenoid 124, air exit gauze 130, a modified analyser spring holder 131 and a loading funnel 120 comprising a funnel discharge orifice 126 and three air jet pipe stubs 125;

ii) a sample handling means comprising a hopper 140, a hopper exit 141, a feed tray 142, a feed tray lip 143 and a feed tray exit 144; and iv) a tapered spring 150.

The disengagable drive means allows the flexible coupling 15, that was shown in FIG. 1, to be eliminated. This elimination is preferable as otherwise the flexible coupling 15 damps the oscillations of the oscillatory assembly. FIG. 11 shows the disengagable drive means in its disengaged position. A primary gear 101, connected to the stepper motor shaft 100, is used to rotate the secondary gear 104, and hence the extender shaft 11, via either a first intermediate gear 102 or a second intermediate gear 103, which are used as idlers for anticlockwise or clockwise rotation, respectively, of the secondary gear 104. In the disengaged position the clearance between the first and second intermediate gears 102, 103 and the secondary gear 104 is sufficient to allow oscillations of the oscillatory assembly without the secondary gear 104 coming into contact with either of the two intermediate gears 102, 103. The first and second intermediate gears 102, 103 are held in engagement with the primary gear 101 by means of an idler frame 105a, b. The intermediate gears are mounted in this idler frame by means of the first and second idler shafts 106, 108. The idler frame 105 is mounted on the stepper motor shaft 100 and thus rotation of the stepper motor shaft 100 causes the idler frame 105 to rotate, however, the coupling between the stepper motor shaft 100 and the idler frame 105 is by friction. Thus, in the absence of obstructions, the idler frame 105 will rotate with the stepper motor shaft 100 but if the idler frame 105 is obstructed then the stepper motor shaft 100 may rotate independently of it.

For example, when the disengagable drive means is in the disengaged position and it is desired to rotate the secondary gear 104 in a clockwise direction, there are three steps to perform the desired rotation:

i) engagement of the second intermediate gear 103 with the secondary gear 104;

ii) clockwise rotation of the primary gear 101 and the secondary gear 104; and iii) disengagement of the second intermediate gear 103 from the secondary gear 104.

The engagement step (i) is performed by rotating the stepper motor shaft 100 in a clockwise direction for a predetermined number of steps. The idler frame 105 will, due to the friction between it and the stepper motor shaft 100, rotate with the stepper motor shaft 100 and will therefore bring the second intermediate gear 103 into engagement with the secondary gear 104.

Continued clockwise rotation of the stepper motor shaft 100 will cause clockwise rotation of the secondary gear 104 via anticlockwise rotation of a second intermediate gear 103. This is because the idler frame 105 cannot rotate any further clockwise, due to the engagement of the second intermediate gear 103 with the secondary gear 104, and therefore continued rotation of the stepper motor shaft 100 will overcome the friction between it and the idler frame 105 to produce rotation of the second intermediate gear 103 and the secondary gear 104.

Once the secondary gear 104 has been rotated clockwise sufficiently, the second intermediate gear 103 may be disengaged from it so that oscillations of the oscillatory assembly may be established without interference. Disengagement is effected by rotating the stepper motor shaft 100 anticlockwise by the same predetermined number of steps as were earlier used for engagement. Although the idler frame 105 is prevented from rotating clockwise by the second intermediate gear 103, the idler frame 105 is not prevented from rotating anticlockwise and thus the friction coupling between it and the stepper motor shaft 100 will cause the idler frame to rotate anticlockwise by the predetermined number of steps. (Continued anticlockwise rotation of the stepper motor shaft 100 would eventually cause the first intermediate gear 102 to engage with the secondary gear 104.)

Anticlockwise rotation of the secondary gear 104 is performed in a similar manner as described above, with anticlockwise rotation of the stepper motor shaft 100 being used to engage the first intermediate gear 102 with the secondary gear 104, continued anticlockwise rotation being used to rotate the secondary gear 104 anticlockwise, and clockwise rotation of the stepper motor shaft 100 being used to disengage the first intermediate gear 102 from the secondary gear 104 and to return the disengagable drive means to the disengaged position.

The particles are loaded into the analyser spring 3 by a loading funnel 120, which is movable between a loading position, in which particles may be transferred into the analyser spring 3, and a default position. FIG. 11 shows the loading funnel 120 in the default position in which the funnel discharge orifice 126 is sufficiently clear of the inlet funnel 2 to allow oscillations of the oscillatory assembly without contact between the funnel discharge orifice 126 and the inlet funnel 2, and also shows one end of the analyser spring 3 supported by the modified analyser spring holder 131. The loading funnel 120 is moved to the loading position by energising the support arm solenoid 124 thereby attracting the support arm solenoid core 123. The energisation overcomes a spring (not shown) and thus the support arm solenoid core 123 is able to pull down the funnel support arm 121 so that the funnel discharge orifice 126 engages with the inlet funnel 2. Particles are transferred into the analyser spring 3 with a blast of air, supplied via the air jet pipe stubs 125, which entrains the particles within the airflow and transfers them into the analyser spring 3. (Note: there are three air jet pipe stubs 125 spaced circumferentially around the loading funnel 120 at 120° intervals. One of the air jet pipe stubs 125 is not visible as it is obscured by the loading funnel 120.) The modified analyser spring holder 131 incorporates the air exit gauze 130 which allows the blast of air to pass through the analyser spring 3 to the atmosphere whilst preventing entrained particles from escaping the analyser spring 3. As an alternative to the use of a gauze 130, or in cases where a gauze 130 has become blocked by trapped particles, the spring may be slightly extended during transfer of particles from the funnel 2 so that the transporting air can escape between the coils of the spring. This may however lead to a loss of some of the finest particles from the powder sample prior to measurement.

The sample handling means in this embodiment constitutes a vibratory feeder. When the vibrations are energised, particles leave the hopper 140 via the hopper exit 141 and pass along the feeder tray 142, constrained by the feeder tray lips 143, to the feeder tray exit 144. The particles then fall from the feeder tray exit 144 into the loading funnel 120. Two benefits of using a vibratory feeder for the sample handling means are that the quantity of particles transferred into the loading funnel 120 may be accurately controlled and that particles do not tend to segregate according to their size. The quantity of particles discharged into the loading funnel 120 may be controlled by setting the amplitude, frequency or duration of the vibratory feed.

A quantity of particles corresponding to a single analysis may be loaded into the hopper 140, or alternatively the hopper 140 may be filled with particles and samples may be repeatedly loaded into the analyser spring 3 until measurements have been performed on the entire contents of the hopper. The latter method allows the problem of particle segregation to be overcome, should this be a problem. The particle sample may be a sample taken from a product stream in an industrial process where the analyser results are used for process control.

The embodiment of FIG. 11, when compared to FIG. 1, shows that the reed spring 19 (which was a rectangular strip of metal) has been replaced by the tapered reed spring 150. The tapered reed spring 150 is tapered in both width and thickness from the reed spring support 20 to the pivot axis 23 and has been found to improve the mass/resonant frequency sensitivity as well as the accuracy with which the resonant frequency of the oscillatory assembly may be measured, by improving the Q-factor of the oscillatory assembly. Desirable material properties of the tapered reed spring 150 are that it should have a high Young's modulus E, a low density $\rho$, a low coefficient of thermal expansion and a low thermo-elastic coefficient TEC. A preferred material from which to construct the tapered reed spring 150 is the alloy NiSpan-C available from Inco Alloys International. Other materials, for example ceramics such as quartz, are also suitable butmay be more difficult to manufacture.

Figure 12A:
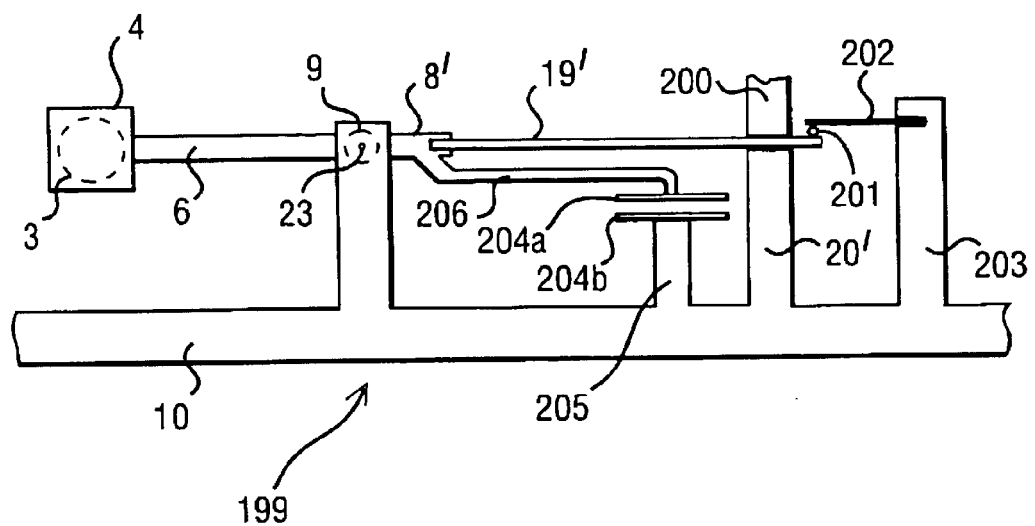
FIG. 12a is a schematic side elevation view of an apparatus according to a third embodiment of the invention, and is illustrated in a mode of operation for agitating particles within the coiled spring.
Figure 12B:
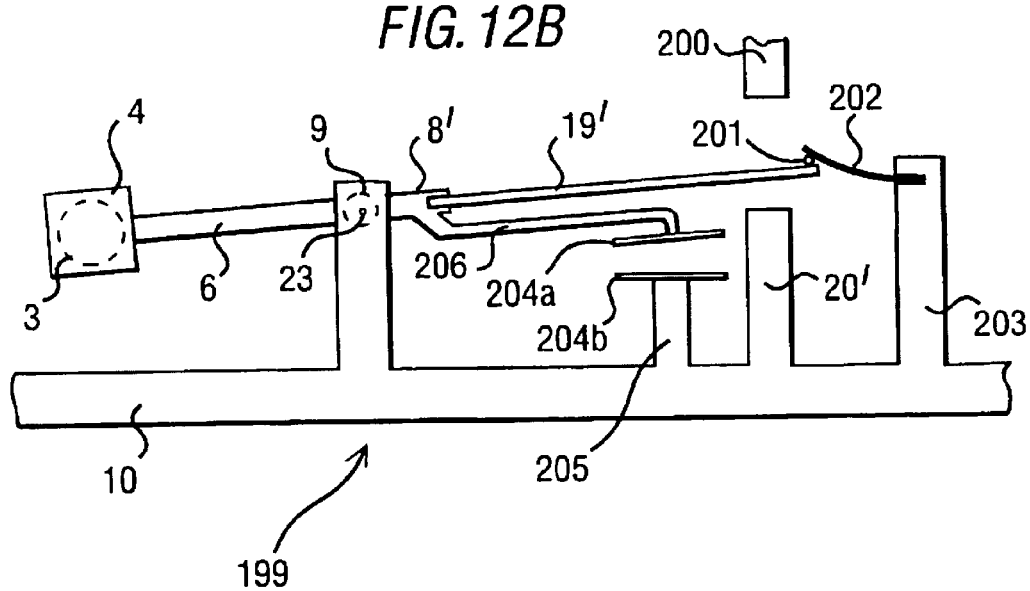
FIG. 12b shows the apparatus of FIG. 12a in a mode of operation for weighing particles within the coiled spring.

FIGS. 12*a* and 12*b* show a third and preferred embodiment 199 of the invention. Whereas the first and second embodiments used the same reed springs 19, 150 for agitating and for measuring the mass of particles within the analyser spring 3, the third embodiment 199 uses a releaseable reed spring 19' for agitating the particles and a separate measurement reed spring 202 for measuring the mass of the particles within the analyser spring 3. The third embodiment 199 is operated in two distinct modes: an agitation mode for agitating particles inside the analyser spring 3 and a measurement mode for measuring the weight of particles inside the analyser spring 3. A further difference is that the mass of the particles is measured under static conditions.

FIG. 12*a* shows the third embodiment 199 in the agitation mode of operation. For clarity some of the components have not been illustrated. Those components that correspond to components shown in FIGS. 1 and 11 have retained the same reference numerals.

The releaseable reed spring 19' is held at one endby a modified T-piece 8' and at the other end by a modified reed spring support 20' in conjunction with a reed spring clamp 200. In the agitation mode the reed spring clamp 200 is urged towards the modified reed spring support 20 thereby clamping the releaseable reed spring 19' to the modified reed spring support 201.

The reed spring clamp 200 is actuated by a linear actuator (not shown) comprising a threaded shaft, an electric motor and a threaded nut. The nut is mounted on the shaft and is free to move axially along the shaft when the shaft is rotated relative to the nut by the electric motor. As an alternative to using a linear actuator, a solenoid may be used to urge the reed spring clamp 200 towards the modified reed spring support 20'.

Once the releasable reed spring 19' has been clamped, vigorous oscillations may be induced in the modified T-piece 8', and hence the analyser spring 3, using a solenoid (not shown) as for the first and the second embodiments.

A capacitive sensor 204 is used to sense the position of the modified T-piece 8'. The lower plate 204*b* of the capacitive sensor is mounted on a capacitive sensor support 205 which projects from the support frame, while the upper plate 204*a* of the capacitive sensor is mounted at one end of a capacitive sensor arm 206. The other end of the capacitive sensor arm 206 connects to the modified T-piece 8'. Angular deflections of the modified T-piece 8' about the pivot axis 23 result in the upper plate 204*a* of the capacitive sensor moving relative to the lower plate 204*b*, thereby changing the capacitance between the two plates. The change in capacitance may, for example, be sensed by using the capacitive plates 204*a*, 204*b* as part of an electrically resonant tuned circuit and sensing the frequency shift of the resonance.

Alternatively, frequency may be determined by monitoring the output of a strain gauge positioned on the leaf spring 19'.

An advantage of using the capacitive sensor 204 is that it allows enhanced resolution and repeatability when compared to the infra-red sensor 21 that was used in the first and second embodiments and to strain gauge methods.

FIG. 12*b* shows the third embodiment 199 in its measurement mode of operation. To enter the measurement mode of operation, the oscillation of the T-piece 8' is stopped, and the reed spring clamp 200 is moved away from the modified reed spring support 20' so that the releaseable reed spring 19' is free to move and is no longer restrained against the modified reed spring support 20'. The arrangement of the modified T-piece 8' is such that even without any particles in the analyser spring 3, the moment of the analyser spring 3 and the extender arm 6 about the pivot axis 23 is greater than that of the releaseable reed spring 19' and the capacitive sensor arm 206. Therefore, upon the release of the reed spring clamp 200 the releaseable reed spring 19' will lift off the modified reed spring support 20' and the oscillatory assembly will rotate about the pivot axis 23.

The rotation of the oscillatory assembly is arrested by the releaseable reed spring 19' coming to bear against the measurement reed spring 202 via an intermediary ball 201. The spring constant of the measurement reed spring 202 is lower than that of the releaseable reed spring 19' so that the measurement reed spring 202 is deflected by virtue of the releaseable reed spring 19' bearing against it. As the releaseable reed spring 19' is stiffer, it bends only slightly when compared to the measurement reed spring 202.

The deflection of the measurement reed spring 202 depends upon the movement of the analyser spring 3 about the pivot axis 23. Thus the deflection of the measurement reed spring 202, the rotation of the oscillatory assembly about the pivot axis 23, and the position of the capacitive sensor upper plate 204*a* relative to the lower plate 204*b* will all be proportional to the mass of particles within the analyser spring 3. The mass of powder may be determined from the spacing of the capacitor plates 204, i.e. from the capacitance measured between the plates. Alternatively, the deflection of measurement reed spring 202 may be measured, for example with a strain gauge, to determine the angular position of the oscillatory assembly and hence the mass of powder remaining in the spring.

The intermediary ball 201 is held captive within a small depression (not shown) at the end of the releaseable reed spring 19' distal from the modified T-piece 8'. The use of the intermediary ball 201 has been found to increase the sensitivity of the apparatus and also serves to accurately define the point of contact between the releaseable reed spring 19' and the measurement reed spring 202, as well as to thermally isolate the measurement reed spring 202 from the releaseable reed spring 19'.

An advantage conferred by the embodiment illustrated in FIGS. 12a and 12b is that the releaseable reed spring 19' and the measurement reed spring 202 may be chosen independently of each other. This allows the releaseable reed spring 19' to be selected to give a suitable resonant frequency for the oscillated assembly, and allows the measurement reed spring 202 to be selected to give a large deflection, and hence good sensitivity, when the analyser spring 3 is full of particles.

Figure 13:
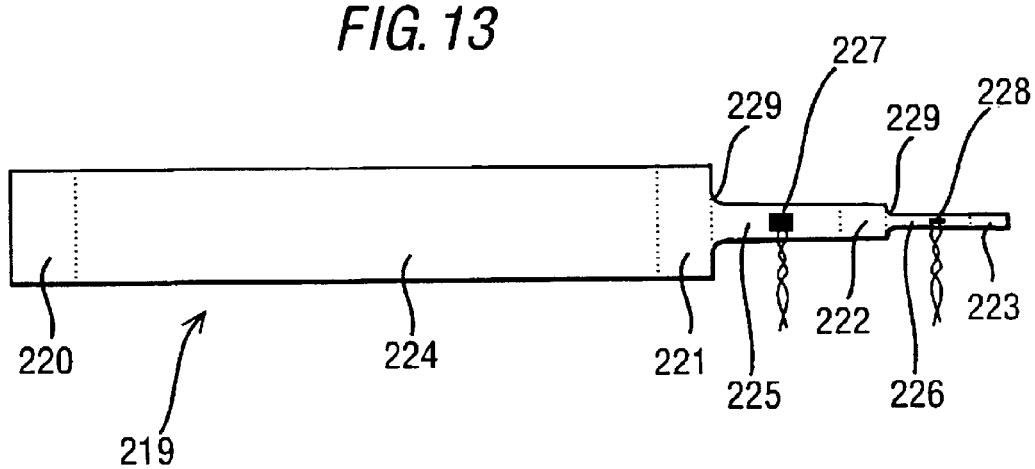
FIG. 13 shows an alternative reed spring which may be used in conjunction with an apparatus similar to that illustrated in FIGS. 12a and 12b.

FIG. 13 shows a stepped reed spring 219 which comprises three spring portions: a reed portion 224, a first measurement portion 225 and a second measurement portion 226.

The stepped reed spring 219 when considered from the 'T-piece end' to the other end comprises the following elements: a T-piece securing area 220, a reed portion 224, a first clamp area 221, a first measurement portion 225 of a first width and stiffness, a second clamp area 222, a second measurement portion 226 of a second width and stiffness and finally a measurement securing area 223. The stepped reed spring 219 is formed from a single piece of metal but the width of the reed and/or optionally its thickness is varied in two steps to provide the three different portions. Radiussed corners 229 are employed where the stepped reed spring 219 changes width (between the first clamp area 221 and the first measurement portion 225 and between the second clamp area 222 and the second measurement portion 226) to prevent localised stress concentrations from causing cracking of the stepped reed spring 219.

The stepped reed spring 219 may be used in conjunction with an apparatus (not shown) similar to that of the third embodiment 199. The similar apparatus comprises a first clamp corresponding to clamp 200 of FIG. 12 for clamping the first clamp area 221. When the first clamp area 221 is clamped, the reed portion 224 performs a similar function to the reed spring 19 of the first embodiment and allows particles to be agitated. The apparatus also comprises a second clamp spaced further from axis 23 for clamping the second clamp area 222, and a third clamp for clamping the measurement securing area 223. When the apparatus is in its measurement mode (with the particles not being oscillated) the second clamp allows the selection of either the first measurement portion 225 or the second measurement portion 226 for a measurement. The first measurement portion 225 is selected by engaging the second clamp, whereas when the second clamp is released then measurement is effected on the basis of the second measurement portion 226.

When the first clamp is released, the oscillatory assembly of the similar apparatus will rotate about its pivot axis until its moment is balanced by that due to the stepped reed spring 219. The arrangement of the stepped reed spring 219 is such that the reed portion 224 is much stiffer than either the first measurement portion 225 or the second measurement portion 226 and therefore the majority of the deflection of the stepped reed spring 219 will be localised in the first measurement portion 225 or the second measurement portion 226. Furthermore, the first measurement portion 225 is arranged to have a stiffness approximately ten times that of the second measurement portion 226.

The presence of two different measurement portions with different stiffnesses allows the similar apparatus to perform an auto-ranging function and select the most appropriate measurement portion for a given mass of particles within its analyser spring. For example, for masses in the range 0–2 g, the first measurement portion 225 may be used whereas for masses in the range 0–0.2 g the second measurement portion 226 may be used. Use of the second measurement portion 226 allows better accuracy and resolution when measuring weights in the range 0–0.2 g.

Whichever measurement portion has been selected, the first clamp area 221 remains unclamped so that the moment of particles in the analyser spring is transmitted to the first measurement portion 225 via the reed portion 224. If the first measurement portion 225 only is being used, then the second clamp is used to clamp the second clamp area 222 and the deflection of the first measurement portion 225 is sensed by a first strain gauge 227. If the second measurement portion 226 is to be used then the second clamp is released from the second clamp area 222 so that the first measurement portion 225 applies a deflecting force to the second measurement portion 226. The resultant deflection of the second measurement portion 226 is sensed by a second strain gauge 228 mounted on the second measurement portion 226. When the second measurement portion 226 is being used it will account for approximately 90% of the deflection of the stepped reed spring 219, the remaining 10% will be due to a deflection in the first measurement portion 225 (there will also be some deflection of the reed portion 224 but as it is much stiffer than either of the measurement portions this deflection will be much smaller) each measured deflection amount of the portion 226 will correspond to an angular position of the oscillatory assembly, and to a unique mass of powder within the spring.

Figure 14:
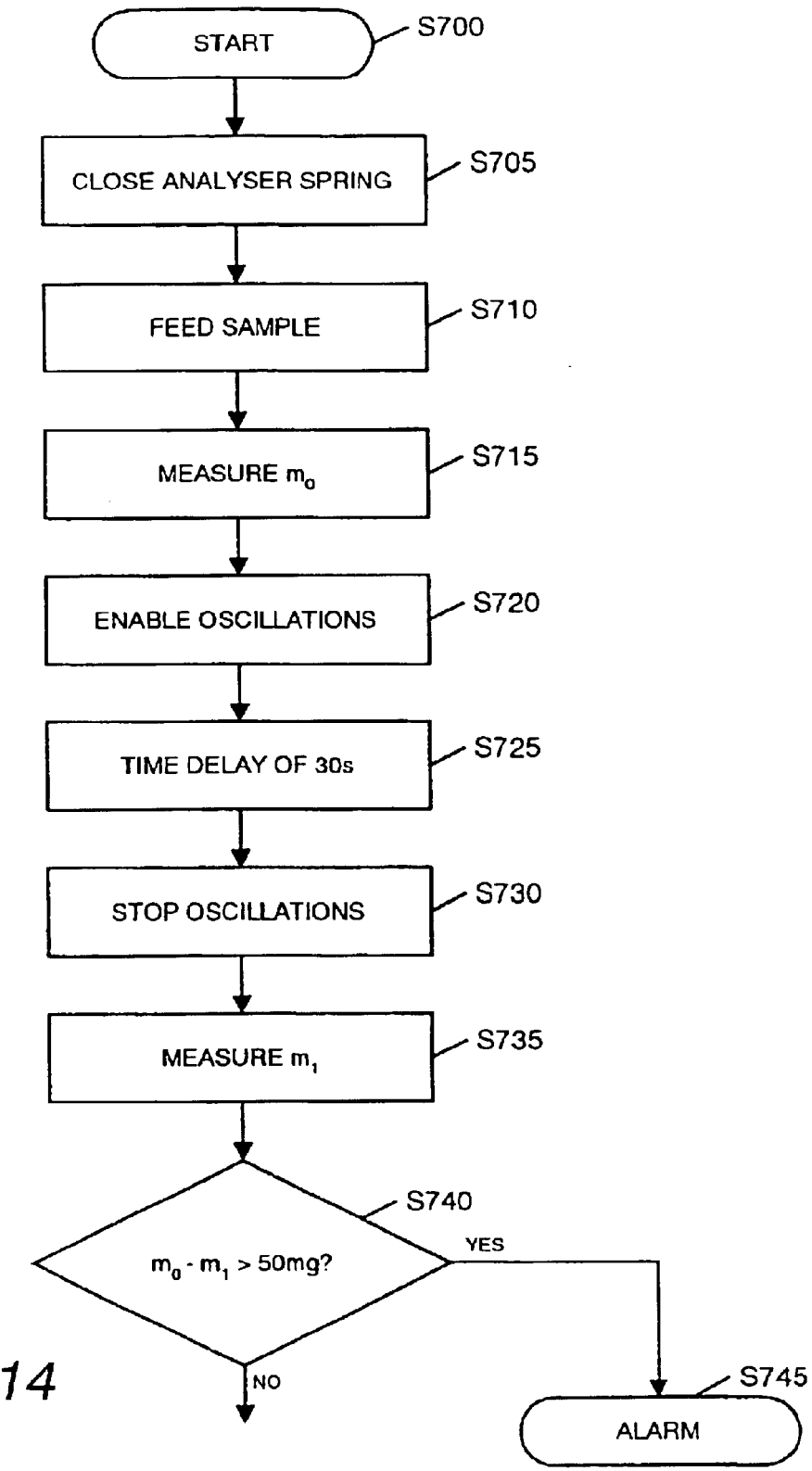
FIG. 14 is a flowchart of a procedure for checking if particles have become trapped between adjacent turns of the coiled spring.

FIG. 14 shows the flowchart of a procedure for checking whether particles have become trapped between adjacent turns of the analyser spring 3. Trapment of particles in the analyser spring 3 is a potential problem as the trapped particles can prevent the analyser spring 3 returning to its coil-bound condition, with the result that particles of a size smaller than the trapped particles may escape even when the analyser spring 3 is nominally returned to its coil-bound condition. This can result in a systematic under-measurement of the weights of the smaller particle size ranges.

The procedure illustrated in FIG. 14 checks for the presence of trapped particles by measuring the weight of particles in the nominally coil-bound analyser spring 3 both before and after a period of agitation; a difference between the two measured values indicates that particles smaller than the trapped particle have escaped the analyser spring 3.

Step 700 is the start of the procedure and it is assumed that the analyser spring 3 is motionless. At step 705 the extender arms 6 are retracted so that the analyser spring 3 is returned to its nominally coil-bound condition. A test sample of particles to be analysed is introduced into the analyser spring 3 at step 710, for example using the apparatus of the second embodiment. A first measurement, $n_0$, is made at step 715 and may be made using the dynamic measurement methods of the first and second embodiments or the static measurement method of the third embodiment. Step 720 starts vigorous oscillations of the analyser spring 3 so that, if there is a particle trapped, particles smaller than this will be able to exit the analyser spring 3. Step 725 is a time delay of 30 seconds, for example, during which oscillations are maintained before being stopped at step 730. At step 735 a second measurement, $m_1$, is made of the mass of particles. Step 740 evaluates the expression $m_0-m_1$ and compares this to a threshold value of, for example, 50 mg. If the weight of powder within the analyser spring 3 has decreased by more than the threshold value as a result of the oscillations during the time delay, then control passes to step 745 which raises an alarm so that an operator may clean the analyser spring 3. One way of cleaning the analyser spring 3 is to extend it and then brush in-between the adjacent turns to dislodge any trapped particles. If $m_0-m_1$ is less than 50 mg then it is assumed that no particles are trapped and control is then passed to a measurement procedure, for example those illustrated in FIG. 3, 4 or 5.

Various modifications to the above-described apparatus and methods may be made without departing from the invention.

Figure 15:
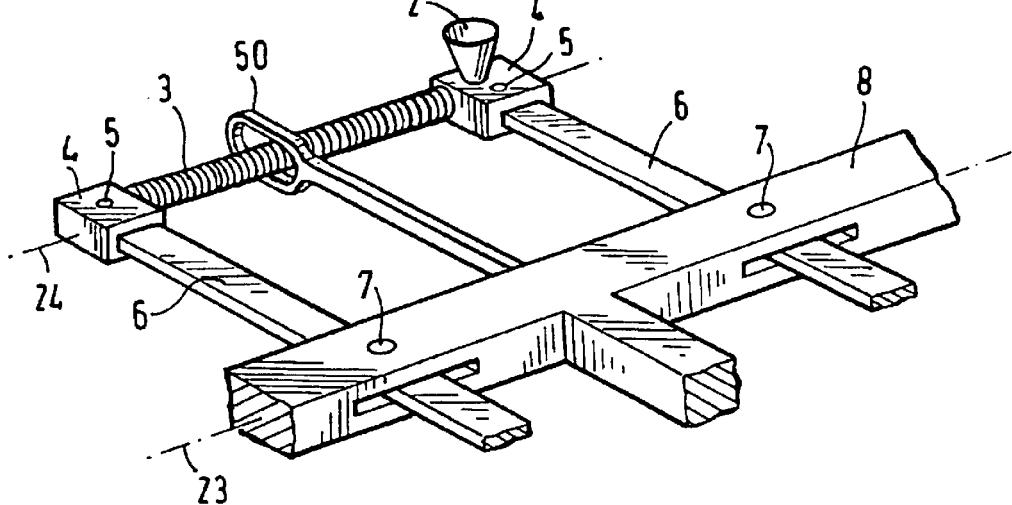
FIG. 15 is an isometric view of the coiled spring and a spring support to reduce transverse oscillations of the coiled spring.

In the embodiments described the analyser spring 3 is supported by an analyser spring holder 4 at each end. However, some operating conditions may cause the central region of the analyser spring 3 to move, relative to the analyser spring holders 4, in a direction transverse of the longitudinal axis of the analyser spring 3. Such motion may cause an excessive, periodic, extension of the analyser spring 3 causing an uncertainty as to the actual spacing of the coils of the analyser spring 3. The resultant uncertainty as to the size of particles able to escape the analyser spring 3 reduces the discrimination of the particle size analyser 1. Transverse motion of a central portion of the analyser spring may be reduced by using an analyser spring support 50 as shown in FIG. 15. The analyser spring support 50 will reduce the tendency but in effect creates two new analyser spring sections, each of which will be susceptible, though to a reduced extent.

The reason for such transverse motion is that energy from the motion of the oscillatory assembly, of which the analyser spring 3 is a part, may be coupled to the analyser spring 3 if the oscillatory frequency of the oscillatory assembly is similar to a resonant frequency of the transverse motion of the analyser spring 3. If the frequencies are not similar then the degree of coupling will be small and the transverse motion of the analyser spring 3 will be, correspondingly small. It is thus beneficial if the resonant frequency of the oscillatory assembly is not near to the fundamental, or harmonics, of the frequency at which the analyser spring will transversely vibrate, in order to minimise any coupling. This may be accomplished by at least one of either changing a characteristic of the spring, e.g. wire diameter, or changing the resonant frequency of the oscillatory assembly. An alternative solution to the problem of coupling is to mathematically model the induced motion of the analyser spring 3 and use this as a correcting factor in the determination of the mass of particles remaining within the analyser spring 3.

The analyser spring 3 may be either a coil-bound or a close-coiled spring. The analyser spring 3 is preferably made from a material, for example high carbon steel, with a high Young's modulus E and a low density ρ in order to maximise the sensitivity of the particle size distribution analyser to the relatively small mass of the particles within the analyser spring; a low coefficient of thermal expansion is also desirable. A coil-bound spring is able to give a discrimination of smaller particles than a close-coiled spring. However, if the smallest particles are not of interest and do not need to be retained within the spring then a close-coiled spring may be used, provided that the gap between adjacent turns in the unextended state is smaller than the smallest particle size of interest. Springs which have a finite residual stress in their unextended state have been found to provide more uniform spring coil opening when stretched.

Non-uniformity between different portions of the analyser spring 3 is a limitation on the ability of the particle size distribution analyser to discriminate between particles of different sizes and is also a limitation as to the smallest particles that may be satisfactorily measured. This is because non-uniformity can result in the gap between adjacent turns having a different size in different regions of the analyser spring 3. Thus a particle that is nominally too large to fall out of the analyser spring 3 may, during vibro-fluidisation and agitation, come upon a region with a larger gap and may fall out there. This effect is particularly significant for a coil-bound spring that has been extended slightly from the coil-bound condition as the effect is proportionately greater for small particles and this forms a limitation as to the smallest particles that may be analysed.

Particles, for example 2 mm diameter ballotini spheres, may be placed within the analyser spring 3 in order to promote the vibro-dispersion and to reduce agglomeration of the test powder. These particles may advantageously be rendered captive by ensuring that the gap between adjacent turns of the analyser spring never becomes so large as to allow their discharge.

An analyser spring that is neither coil-bound nor close-coiled may be used by first longitudinally compressing it to either a coil-bound or close-coiled condition. A sample of particles may then be introduced into the analyser spring, and the analyser spring oscillated and extended as before.

The embodiment of FIG. 1 shows an inlet funnel 2 in order to introduce the test powder to the analyser spring 3. Other arrangements are also possible, for example, in some circumstances it may be more convenient to remove the analyser spring 3 for the introduction of a test powder and then replace it in the particle size distribution analyser 1 for analysis.

In the embodiments described hitherto, the actuation of the extender arms 6 is by means of a extender shaft 11 with two oppositely-handed threaded sections 12. Alternatively, one movable extender arm 6 could be used in conjunction with a fixed extender arm (not shown) on the T-piece 8. Other mechanisms are also possible, for example, a rack and pinion may be used to effect extension of the analyser spring 3. The preferred embodiment calculates the extension of the analyser spring 3 on the basis of the rotation of the extender shaft 11 from a datum position, which rotation corresponds to an extension of the analyser spring 3. This datum position may conveniently be, in the case of a coil-bound spring, the extension at which the analyser spring 3 cannot be further compressed. For a close-coiled spring, the datum position may, for example, be defined with a "home" position sensor to define a fixed datum and hence extension.

Instead of using the disengagable drive means of FIG. 11, other means for achieving the same result are possible. For example, the stepper motor shaft 100 could instead be connected by a flexible coupling to a primary shaft having a primary gear, this primary gear would be engageable/disengagable with the secondary gear 104 under the control of a solenoid which would produce angular movement of the primary shaft axis relative to the stepper motor shaft 100 axis. Yet another alternative is to use a non-contact means of rotating the extender shaft 11, instead of a disengagable drive means. For example, a pancake induction motor could be formed by replacing the secondary gear 104 with an aluminium disk and providing electromagnets in proximity to the disk. Suitable energisation of the electromagnets would produce a rotating magnetic field about the extender shaft 11, which would induce a back e.m.f., and hence torque, in the aluminium disk. The use of such a motor would require, for example, a shaft encoder to determine the rotation of the extender shaft 11.

Hitherto, two similar embodiments have been described:
(i) the third embodiment of FIGS. 12*a* and 12*b*, and
(ii) the apparatus (not shown) described in relation to the stepped reed spring 219 of FIG. 13;

in both these cases deflections of a measurement reed spring were caused by using an "oscillation" reed spring to bear upon the measurement reed spring. In case (i) the "oscillation" reed spring was separate and in case (ii) the "oscillation" reed spring was integral with the measurement reed spring.

In a further embodiment, an "oscillation" reed spring and a measurement reed spring are each attached to a modified T-piece. The measurement reed spring spans from the modified T-piece to a modified reed spring support whilst the "oscillation" reed spring spans from the modified T-piece to a reed spring support and reed spring clamp. Thus motion of the modified T-piece about its pivot axis is always resiliently opposed by the measurement reed spring, whilst motion of the modified T-piece is only resiliently opposed by the "oscillation" reed spring when the reed spring clamp clamps the "oscillation" reed spring to its reed spring support.

With this further embodiment, to form vigorous oscillations of powder within an analyser spring the reed spring clamp is engaged so that rotation of the modified T-piece is resiliently opposed by both the "oscillation" reed spring and the measurement reed spring. A solenoid may then be used to induce oscillations. The measurement reed spring must be capable of experiencing the vigorous oscillations without sustaining damage. When the mass of particles within the analyser spring is to be determined, the reed spring clamp is released so that the moments of the particles within the analyser spring causes a deflection of the measurement reed spring and causes the "oscillation" reed spring to lift up from the reed spring support. The deflection of the measurement reed spring is proportional to the mass of particles within the analyser spring.

Furthermore, this further embodiment does not use a linear actuator but instead provides a ferromagnetic portion at the end of the reed "oscillation" spring distal from the modified T-piece. The modified reed spring support is arranged to comprise an electromagnet which may be magnetised by passing an electric current through it. The reed spring clamp of this further embodiment is engaged by passing a current through the electromagnet so that the ferromagnetic region of the "oscillation" reed spring is securely engaged with the modified reed spring support. Note that although the "oscillation" reed spring is always physically connected to the modified T-piece, the reed spring only functions when it is engaged to the modified reed spring support.

In another variation of this further embodiment a single reed spring is used which may have its spring constant changed between two values (a higher value for performing oscillations of the oscillator assembly and a lower value for measuring the mass of particles within the analyser spring). One way of varying the spring constant of the reed spring would be to vary its effective length. With reference to FIG. 1, the effective length of the reed spring 19 could be changed by allowing the reed spring support 20 to be moved between two or more positions relative to the reed spring slide 25. With the reed spring support 20 near the T-piece 8 the reed spring 19 will have a high effective stiffness suitable for agitating powder within the analyser spring 3. By moving the reed spring support 20 a sufficiently long way away from the T-piece 8, the reed spring 19 will have a low effective spring constant suitable for measuring the weight of particles in the analyser spring 3 by detecting the static deflection of the reed spring 19. Another way of providing a spring with a variable spring constant would be to use an electromagnet to emulate a spring and to vary the electric current of the electromagnet so as to vary its effective spring constant.

The stepper motor 16 could be replaced with a DC motor and a shaft encoder with which to determine the rotation produced by the DC motor, and hence the extension of the analyser spring 3. Alternatively, the extension of the analyser spring 3 could be directly measured, for example, using a linear displacement transducer. The use of an electrically conducting analyser spring 3 in conjunction with electrically insulating test powders would allow its extension to be determined by measuring the attendant change in inductance, for example, as part of a resonant tuned circuit.

Although the embodiments described hitherto show the analyser spring 3 and the reed spring 19 on opposite sides of the pivot axis 23, this arrangement could optionally be changed to one where the pivot axis 23 is at one end of the T-piece 8, and with the analyser spring 3 and the reed spring 19 on the same side of the pivot axis 23.

Figure 16:
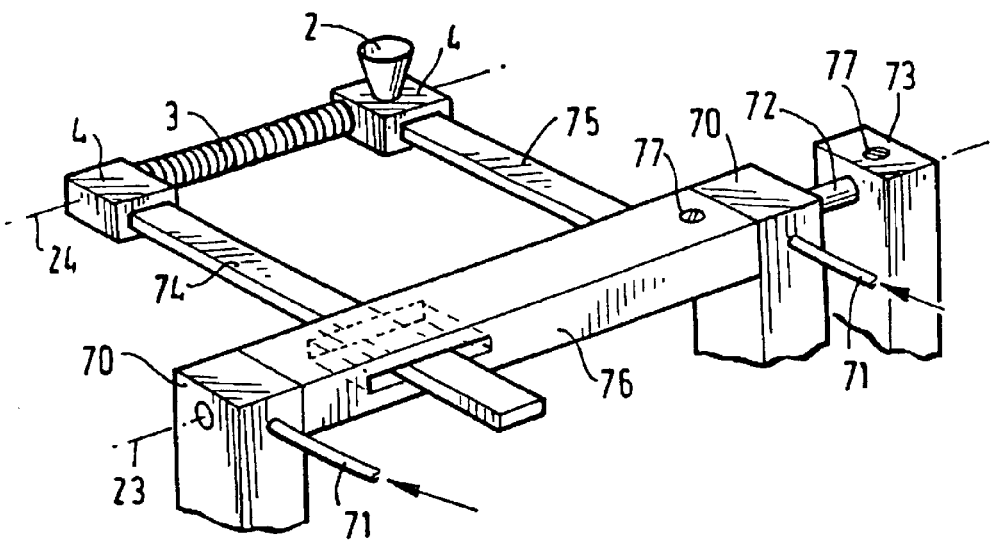
FIG. 16 is an isometric view of an embodiment of the invention wherein a torsion spring restoring means, sliding extender means and an air bearing pivotal axis are combined.

FIG. 16 shows an alternative embodiment of the invention in which an alternative T-piece 76 is supported by two airbearings 70. A supply of compressed air (not shown) feeds the two airbearings via the tubes 71, these airbearings 70 allow the modified T-piece 76 to rotate freely whilst preventing transverse movement and endfloat. The analyser spring 3 is supported at one end by a fixed extender arm 75 and is extended with a sliding extender arm 74 which slides within the alternative T-piece 76 in the longitudinal direction of the pivot axis. This arrangement ensures that the spacing between the axis of the spring and the pivot axis remains constant as the spring is extended, and thus any change in the moment of inertia of the oscillatory assembly is directly attributable to the change in the mass of powder within the spring. The restoring means is a torsion spring 72, fastened by two grub screws 77, which urges the oscillatory assembly towards a datum position. One end of the torsion spring 72 is connected to the alternative T-piece 76 and the other end is held by the torsion spring support 73.

In general, the cone and cup bearings 9 and the air bearings 70 may be replaced by other types of bearings provided these offer low, and relatively constant, friction. Although the embodiments of FIGS. 1 and 11 have shown a biasing means (23, 27, 28) at each end of the T-piece 8, a single biasing means could be used instead. Furthermore, in another alternative embodiment, a cantilevered reed spring is, in addition to providing the restoring means, used to support the T-piece instead of bearings. In this case, the path followed by the analyser spring 3, during oscillations, of the vibratory assembly, will no longer be part of a circle except at low amplitudes when the motion will approximate a circular arc.

In addition to the tapered reed spring 150 and the rectangular reed spring 19, other shapes may also be used. For example, the spring may taper from each end to a narrower central waist or may taper from a wider central region to each end. Other cross sections, for example "V" or "I" may also be used.

In the second embodiment, a tapered reed spring 150 is used to provide the restoring means to urge the T-piece 8 towards the datum position. In an alternative embodiment, each of the cup and cone bearings 9 is replaced with a torsion spring to merge the restoring and bearing functions. An alternative means of providing a restoring force acting towards the datum position is to use two appropriately shaped magnetic fields to repel a magnetic pole attached to the T-piece 8 towards the datum position.

In the embodiments hitherto described, an infrared displacement transducer 21 provides an analogue signal to represent the position of the reed spring 19/150, and hence of the T-piece 8. There are also other types of sensors which could be used to measure the displacement, for example, capacitive or inductive proximity sensors. As an alternative, instead of measuring the displacement, the velocity and/or the acceleration of any of either the analyser spring 3, the T-piece 8 or the reed spring 19 could be measured to infer the displacement. Furthermore, the position of the T-piece 8 could be determined, for example, by measuring the strain in the reed spring 19 with a strain gauge or by measuring the force with which the reed spring 19 reacts against the reed spring support, 20. Digital position sensors, for example of the broken beam type or rotary encoders, could be used instead of the infrared displacement transducer 21. Any of these sensor types may be used in combination.

In the embodiment of FIG. 11, air jet pipe stubs 125 are used to entrain particles in the loading funnel 120, and transfer them downwards into the analyser spring 3. In an alternative embodiment, a pulsating, continuous or intermittent blast of air may be supplied via a jet pipe (not shown) entering from the top of the loading funnel 120 and terminating substantially centrally within the discharge orifice 126.

Figure 17:
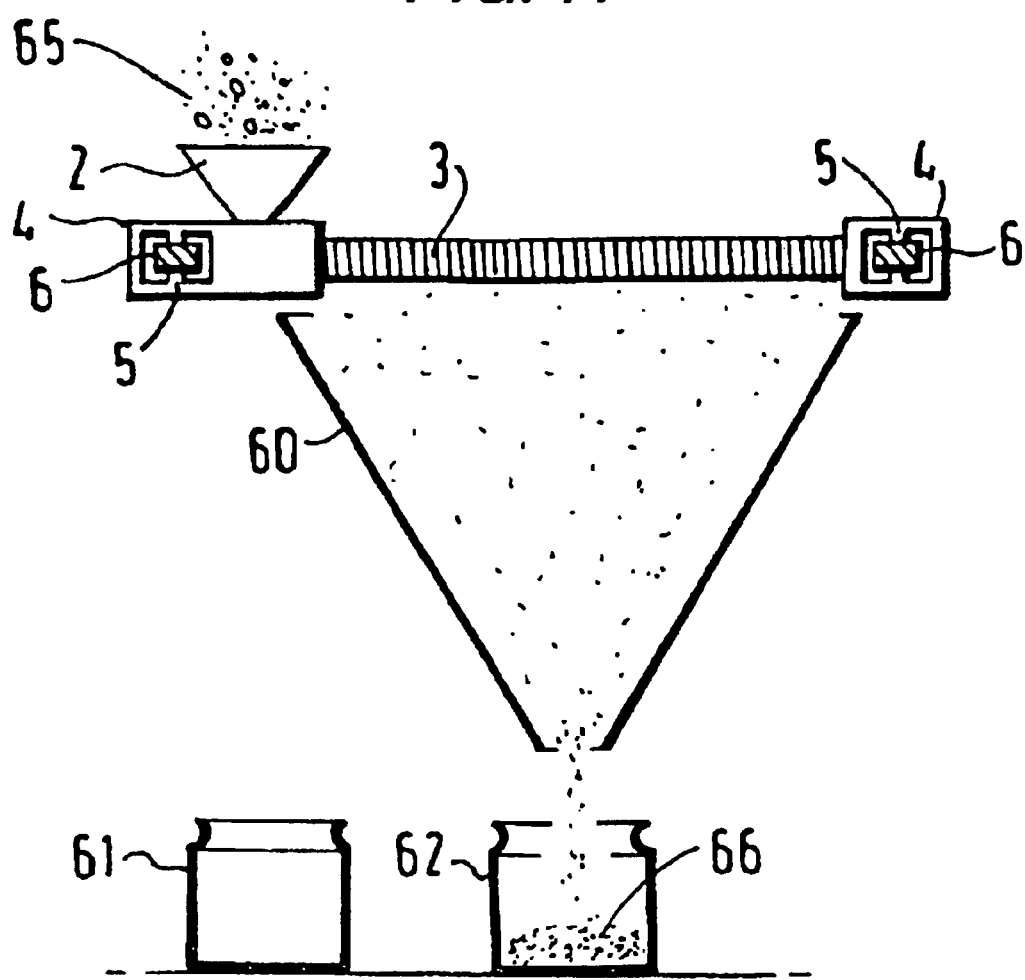
FIG. 17 is an elevation view of the coiled spring and apparatus for collecting size fractions.

In the embodiment of the invention as described above and illustrated in FIG. 1, no attempt is made to collect the test powder emanating from the analyser spring 3. An alternative embodiment which collects the test powder released from the analyser spring 3 is shown in FIG. 17. This embodiment allows the separation of a test powder 65 into different fractions according to particle size. Particles leaving the analyser spring 3 are directed by a funnel 60, which is preferably vibrating, into a container 62. This container 62 will receive the particle fraction 66 that is able to escape through the gaps in the analyser spring 3. A different fraction may be collected by placing a different container 61 underneath the funnel 60 and extending the analyser spring 3 so that a new fraction, consisting of larger particles than the previous fraction, may be collected.

Whereas FIGS. 7a and 7b illustrated a flowchart of an adaptive measurement procedure for use in conjunction with the first or second embodiments, a similar procedure maybe used in conjunction with the third embodiment. In FIG. 7 the amplitude of the oscillations was changed between vigorous oscillations and gentle oscillations, at steps 430 and 440. A similar procedure for use in conjunction with the third embodiment would amend the following steps:

(i) step 430 would be replaced by steps to engage the reed spring clamp 200 and then enable vigorous oscillations of the analyser spring 3, (ii) steps 440 and 442 would be replaced by steps to stop oscillations and then disengage the reed spring clamp 200 from the releaseable reed spring 19'.

A similar procedure may also be modified so that instead of performing a maximum of ten iterations around the loop, control may be arranged to pass from step 450 to step 430 indefinitely until the mass difference between consecutive measurements is less than a threshold. A suitable threshold is 50 mg.

In situations where the separation of a test sample into different size fractions, rather than determining the mass of each fraction, is the aim, particles may be carried in a non-solvating liquid. For example, hygroscopic particles could be shielded from atmospheric moisture using oil. Alternatively, a damp powder could be dried prior to, or during, measurement by passing an electric current through the analyser spring 3.

The methods of operation associated with FIGS. 3 and 4 returned the analyser spring 3 to the coil-bound position, at steps S130 and S235 respectively, prior to measuring the mass of particles within the analyser spring 3. These steps could be omitted although their omission could cause measurement inaccuracies, as explained regarding FIG. 5, due to the change in the behaviour of the analyser spring 3 while it is being extended out of the coil-bound condition.

Figure 18:
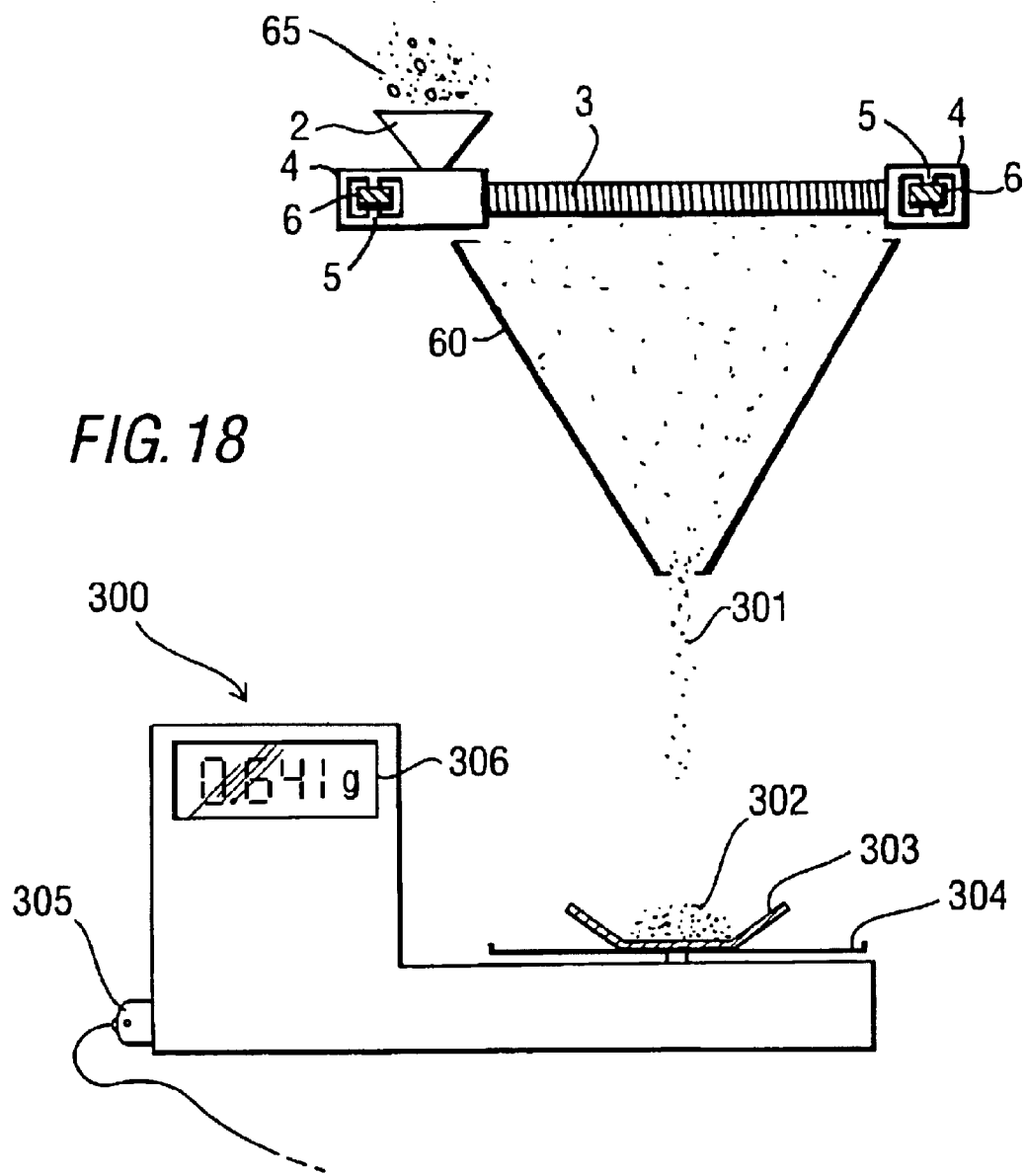
FIG. 18 is an elevation view of an apparatus in which the weight of particles that leave the coiled spring is measured using an electronic weighing scale.

FIG. 18 shows an embodiment in which the test powder released from the analyser spring 3 is collected by an electronic weighing scale 300. This allows the mass of particles which have been released from the analyser spring 3 to be measured without measuring a characteristic of the oscillated assembly. This embodiment may be used with the first, second or third embodiments described earlier. Components in common with FIG. 17 have the same reference numerals.

Falling particles 301 emanating the funnel 60 are collected by a receptacle 303 on which a small pile of collected particles 302 is illustrated. The receptacle 303 is positioned on a weighing scale pan 304 and the electronic weighing scale 300 displays the weight of the collected particles 302 on a display 306. The electronic weighing scale 300 may be arranged to auto-zero and hence ignore the mass of the receptacle 303. Also shown is a data transfer lead 305 which may be used to connect the electronic weighing scale 300 to the particle size analysis apparatus. With reference to the micro controller 33 shown in the system of FIG. 2, data may be transferred from the electronic weighing scale 300 via the data transfer lead 305 to the micro controller 33 and commands (for example auto-zero) may be sent from the micro controller 33 to the electronic weighing scale 300. Another use for the electronic weighing scale 300 is as part of a calibration routine for the particle size analysis apparatus.

Hitherto, methods of operation of the current invention has been described wherein the frequency at which the oscillatory assembly oscillates is the natural frequency of the oscillatory assembly. The natural frequency of the oscillatory assembly varies with the mass of particles within the analyser spring and this variation may be used to determine the mass of the particles. Alternatively, the oscillatory assembly may be driven at a frequency other than its resonant frequency in which case there will be a periodic variation in the amplitude of the oscillatory assembly at a frequency which is the difference between the driving frequency and the natural frequency of the oscillatory assembly.

Another method with which the mass of particles within the analyser spring 3 may be measured is to monitor the exponential decay of the oscillatory amplitude when the oscillations are not sustained but are instead allowed to decay. Non-sustained oscillations could be produced by disabling the solenoid driver 39 or by applying an impulse to a stationary oscillatory assembly. By measuring the time constant, $\tau$, of the decaying oscillations the damping factor, $\xi$, and hence the mass of particles in the analyser spring 3, could be inferred.

Figure 19:
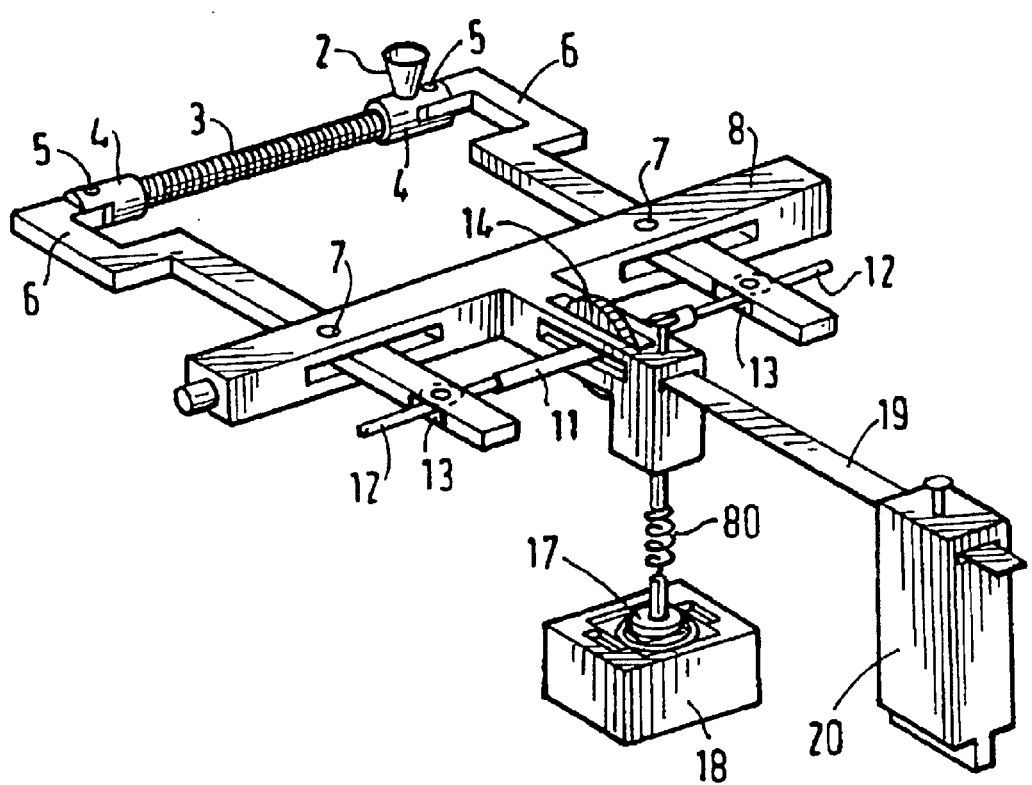
FIG. 19 is a diagram of an apparatus in which the drive means is resiliently coupled to the coiled spring.

In the first, second and third embodiments the driving means, provided by the solenoid core 17 and the solenoid coil 18, is directly connected to the T-piece 8/8' and the supporting frame 10. An alternative embodiment in which both phase and amplitude measurements may be made is one in which the driving means is resiliently coupled to the oscillatory assembly. FIG. 19 shows an apparatus similar to that of FIG. 1 (reference numbers have been used in common, some parts have not been shown for clarity), in which a non-coil-bound helical spring is used as a resilient coupler 80. The resilient coupler 80 allows the T-piece 8/8' to be excited by the driving means whilst oscillating independently of it, in the manner of a resonator weakly coupled to an exciter. This allows the amplitude, the frequency and, relative to the driving means, the phase of the motion of oscillatory assembly to be measured. These three parameters can be processed to provide more accurate mass measurements than an embodiment which uses the resonant frequency of oscillation alone. The resilient coupler 80 connects the solenoid core 17 to the central projection of the T-piece 53. Whereas the solenoid core 17 was previously arranged to exert a force on the central projection of the T-piece 53, in this embodiment, the solenoid core 17 is arranged to take up defined positions in response to the solenoid driver 39. It is desirable that interaction with the resilient coupler 80 should have a minimal effect on the position of the solenoid core 17 (i.e. the position of the solenoid core 17 is solely determined by the solenoid driver 39). After a settling time, during which the transient motion gives way to the steady state motion, the oscillatory assembly will be at the same frequency as the drive means but with a phase shift of e and the amplitude of oscillations will depend on both how close the driving frequency is to the natural frequency and also upon the damping factor $\xi$. The phase shift could, for example, be determined by measuring the time interval for corresponding parts of the oscillatory cycle between the driving means and the oscillatory assembly. When the oscillatory assembly is driven at its resonant frequency, the phase shift $\theta$ between the oscillatory assembly and the drive means will be zero.

Rather than directly measuring the amplitude, an alternative method comprises adjusting one, or both, of the reed spring 19 and the solenoid driver 39, in order to maintain the amplitude of vibration constant as the mass of test powder remaining in the analyser spring 3 reduces. A change in the reed spring 19 could be produced by varying the temperature of the reed spring 19 or by sliding the reed spring support 20 in the reed spring slide 25 in order to change the apparent stiffness of the reed spring 19. Changing the stiffness of the reed spring 19 would also change the resonant frequency of the oscillatory assembly. Alternatively the drive level of the solenoid 17, 18 could be changed by altering either the pulse width or the pulse amplitude produced by the solenoid driver 39. The change in restoring means or drive level required to maintain the amplitude of oscillation constant can then be used to determine the mass of powder remaining in the analyser spring 3.

A further method for improving the measurement accuracy is to take into account the change of distance of the analyser spring axis 24 and extender shaft 11 axis from the pivot axis 23 during extension of the analyser spring 3. This is because, as the two extender arms 6 extend the analyser spring 3, the analyser spring axis 24 and the extender shaft 11 will be brought nearer to the pivot axis 23, with an attendant reduction in the moment of inertia of the oscillatory assembly. This reduction is indistinguishable from that due to a loss of test powder from the analyser spring 3 and therefore needs to be corrected, for example, by calculating the size of this error and removing it from the measured mass of particles remaining within the analyser spring 3 or by calibration. Alternatively, a mechanical compensation arrangement could be used to move a mass away from the pivot axis 23 in correspondence with the motion of the analyser spring 3 towards the pivot axis 23, in order to maintain a substantially constant moment of inertia of the oscillatory assembly.

There are a variety of ways in which the particle size distribution analyser may be calibrated and these in turn affect the way in which the measurement results are interpreted. For example, the measurement scheme of FIG. 3 always performs the measurement step at the same extension of the analyser spring 3. Thus there is no need to take into account the effect that an extension of the analyser spring (as shown in FIG. 6) has on the resonant frequency measured. In this case calibration could, for example, be performed using two different masses within the analyser spring. The mass of a sample of particles within the analyser spring would be derived from the resonant frequency by either interpolating or extrapolating between the two calibration points or alternatively by using a lookup table. Measurements are performed in a variety of different analyser spring extensions in the procedure of FIG. 5 and therefore the calibration data needs to include the effect whereby the extension of the analyser spring 3, as well as the mass of particles within the analyser spring 3, effects the resonant frequency of the oscillatory assembly. The resonant frequency of the oscillatory assembly could be converted into a mass value using either a lookup table or by interpolation, based on calibration data. Mass values based on amplitude and/or phase measurements will, if they are performed at varying analyser spring extensions, also need to take into account the shift in resonant frequency produced as a result of changes of the extension of the analyser spring, as both the phase and amplitude are a function of the resonant frequency.

So far, the embodiments have changed the extension of a helical spring to change the gap between adjacent turns. As an alternative, one end of the helical spring could be rotated relative to the other end (i.e. relative rotation about the analyser spring axis 24) which would open up/increase a gap without changing the extension.

Another alternative is to use, for example, an elastomeric tube provided with either slits or holes instead of a helical spring. The size of the slits/holes may be changed by changing the extension of the elastomeric tube. Although the analyser spring has been shown with a circular cross-section this is not a requirement and other cross-sections may also be used (a tube, if used, also need not have a circular cross-section).

Yet another alternative to a receptacle comprising a helical spring is to use two close-fitting coaxial tubes, wherein each of the coaxial tubes is provided with an opening. An aperture of variable size may be formed from the conjunction of the two openings by adjusting their alignment with respect to each other, for example by relative rotation or axial movement between the two coaxial tubes. Such movement may include telescopically extending or contracting the receptacle so as to slide the inner tube out of or into the outer tube. Thus, a particle trapped within the coaxial tubes may be discharged when the aperture is increased in size sufficiently to allow the particle to pass through the aperture. Preferably, the coaxial tubes may be provided with a plurality of adjustable apertures, for example by providing the inner tube with a plurality of openings for correspondence with respective openings in the outer tube, or by providing a slot in the inner tube for correspondence with a plurality of openings in the outer tube or vice versa. If the tubes have cross-sections other than circular, for example rectangular, then relative movement is limited to axial movement of the tubes. The coaxial tubes need to be sufficiently close fitting that the smallest particles of interest are not inadvertently discharged.

The apparatus may be made more sensitive by increasing the lengths of the extender arms 6 to increase the distance between the analyser spring axis 24 and the pivot axis 23.

What is claimed is:

1. A particle size analysis apparatus (1) comprising:

an oscillatory assembly comprising
   (a) a receptacle (3) for receiving a powder sample, the receptacle having an opening defined therein,
   (b) entry means (2) for introducing a powder sample into the receptacle,
   (c) adjuster means (6, 7, 11, 12, 13) for varying the size of the opening,
   (d) support means (6, 8) for supporting the receptacle,
   (e) bias means (19) operable to urge the oscillatory assembly towards a datum position; and drive means (17, 18) for inducing oscillations of the oscillatory assembly so as to cause a portion of the powder sample to exit from the receptacle through the opening;

characterised in that the oscillations of the oscillatory assembly comprise rotary movements about a pivot axis (23) spaced from the receptacle, and in that the apparatus comprises sensor means (21, 204, 227) for producing a signal indicative of the weight or mass of a powder sample in the receptacle.

2. An apparatus according to claim 1, wherein the sensor means is operable to determine a characteristic of the oscillations of the oscillatory assembly.

3. An apparatus according to claim 2, further comprising means for deducing (33) the mass of a powder sample within the receptacle on the basis of a characteristic of the oscillations of the oscillatory assembly.

4. An apparatus according to claim 3 wherein the means for deducing is implemented using a digital processor that is operable to follow a controlling program and manipulate data.

5. An apparatus according to claim 1, wherein the receptacle (3) has a longitudinal axis (24) which is substantially horizontal during operation of the apparatus.

6. An apparatus according to claim 1, wherein the receptacle (3) has a longitudinal axis (24) which is substantially parallel to the pivot axis (23).

7. An apparatus according to claim 1, wherein the receptacle (3) has a longitudinal axis (24) and a portion (50) of the support means is used to restrict transverse movement of a portion of the receptacle relative to the longitudinal axis (24) of the receptacle.

8. An apparatus according to claim 1, wherein the receptacle (3) is a helical coiled spring, and the opening is defined between adjacent turns of the spring.

9. An apparatus according to claim 8, wherein the helical coiled spring is coil-bound when in an unstretched state.

10. An apparatus according to claim 1, wherein the receptacle (3) comprises two relatively movable casings, each casing being formed with an opening alignable with the opening in the other casing.

11. An apparatus according to claim 10, wherein each casing of the receptacle (3) comprises a plurality of openings.

12. An apparatus according to claim 1, wherein the support means comprises a pre-loaded bearing.

13. An apparatus according to claim 1, wherein the entry means (120, 125, 126) is operable to introduce a powder sample into the receptacle (3) using a flow of fluid.

14. An apparatus according to claim 1, wherein the adjuster means comprises:

an arm (6) for extending the receptacle (3);
   a rotary to linear movement converter (12, 13) for converting rotary motion of a member (11, 15) to linear motion of the arm;
   a rotator (16) for rotating the member; and
   detector means for determining the extension of the receptacle.

15. An apparatus according to claim 14, wherein the detector means is operable to detect rotation of the member (11, 15) in order to determine the extension of the receptacle (3).

16. An apparatus according to claim 15, wherein the rotator (16) is releaseably connectable to the member.

17. An apparatus according to claim 1, wherein the bias means is a reed spring (19).

18. An apparatus according to claim 17, wherein the reed spring (150) is tapered.

19. An apparatus according to claim 1, wherein the bias means has a constant of proportionality between
   (i) an angular deviation of the oscillatory assembly from its datum position, and
   (ii) the degree to which the oscillatory assembly is urged towards its datum position, the constant of proportionality being defined by the degree divided by the deviation.

20. An apparatus according to claim 19, wherein the constant of proportionality may be varied in response to a control signal.

21. An apparatus according to claim 20, wherein the bias means comprises a first spring means (19'), a second spring means (202) and releaseable engagement means (20', 200) for engaging the first spring means with the oscillatory assembly in response to the control signal.

22. An apparatus according to claim 21, wherein the engagement means is a clamp (20', 200), the second spring means (202) has a lower constant of proportionality than the first spring means (19), and the second spring means is only deflected by movement of the oscillatory assembly when the engagement means is disengaged from the first spring means.

23. An apparatus according to claim 21, wherein the second spring means (225) is integral with the first spring means (224).

24. An apparatus according to claim 21, wherein the second spring means is always engaged with the oscillatory assembly.

25. An apparatus according to claim 21, further comprising a third spring means (226) having a lower constant of proportionality than the second spring means (225).

26. An apparatus according to claim 1, wherein the drive means (17, 18) is operable to sustain oscillations of the oscillatory assembly.

27. An apparatus according to claim 1, wherein the drive means comprises a solenoid (18).

28. An apparatus according to claim 1, wherein the sensor means is a capacitive position sensor (204).

29. An apparatus according to claim 1, wherein the receptacle contains captive particles.

30. An apparatus according to claim 1, further comprising means for passing an electric current through the receptacle.

31. An apparatus according to claim 1, further comprising feed means (140, 142) operable to convey a powder sample to the entry means.

32. An apparatus according to claim 31, wherein the feed means comprises a vibratory feeder (142).

33. An apparatus according to claim 1, wherein the drive means is coupled by a resilient coupler (80) to the oscillatory assembly.

34. An apparatus according to claim 1, further comprising means for detecting when the rate at which particles leave the receptacle is substantially zero.

35. An apparatus according to claim 1, further comprising means (60) with which particles of a powder sample (66) discharged from the receptacle may be collected in a container (62).

36. An apparatus according to claim 35, comprising a plurality of containers (62) for collecting respective powder sample size fractions (66).

37. An apparatus according to claim 1, further comprising means for outputting a signal indicative of the signal produced by the sensor means.

38. An apparatus according to claim 1, further comprising control means (33) to direct the size of the opening in response to a signal from the sensor means.

39. An apparatus according to claim 38 wherein the control means is implemented using a digital processor that is operable to follow a controlling program and manipulate data.

40. A method of particle analysis using the apparatus according to claim 1, the method comprising the sequential steps of:
  i) introducing a powder sample into the receptacle (3);
  ii) oscillating the oscillatory assembly at a first amplitude in order to cause particles of the powder sample that are smaller than the opening of the receptacle to exit the receptacle (S225);
  iii) oscillating the oscillatory assembly at a second amplitude lower than the first amplitude (S365); and
  iv) measuring a signal produced by the sensor means (S210) while the oscillatory assembly is oscillating at the second amplitude.

41. A method according to claim 40, further comprising the sequential steps of:
  v) increasing the size of the opening of the receptacle (3) from a first size to a second size larger than the first size; and
  vi) repeating steps ii) to iv) at the second size.

42. A method according to claim 40, wherein the amplitude of oscillations of the oscillatory assembly is changed by varying the power output of the drive means.

43. A method according to claim 40, further comprising the step of varying the constant of proportionality of the bias means.

44. A method according to claim 40, further comprising the step, after the step of allowing particles of the powder sample to exit from the receptacle (S125) but before the associated measuring step (S110), of adjusting the size of the opening back to the first size (S130).

45. A method according to claim 40, further comprising the step of ensuring that substantially all the particles of the powder sample that are smaller than the opening have been discharged from the receptacle (S450) before measuring a signal produced the receptacle (S450) before measuring a signal produced by the sensor means (S465).

46. A method according to claim 40, further comprising the steps of: varying the amplitude of oscillations of the oscillatory assembly (S510), measuring a signal produced by the sensor means (S515), and processing the measured signal (S550) to yield a processed value.

47. A method according to claim 40, further comprising the step of ensuring that the signal produced by the sensor means has stabilised (S625) before measuring the signal produced by the sensor means.

48. A method according to claim 40, wherein the frequency at which the oscillatory assembly is oscillated is the resonant frequency of the oscillatory assembly.

49. A method according to claim 40, wherein the signal produced by the sensor means is indicative of the resonant frequency of the oscillatory assembly.

50. A method of claim 40, wherein the signal produced by the sensor means is indicative of the decay time-constant of the oscillations.

51. A method according to claim 40, further comprising the step of determining whether a particle is trapped in the opening of the receptacle (S740).

52. Processor implementable instructions for controlling a processor to implement the method of claim 40.

53. A storage medium storing processor implementable instructions for controlling a processor to implement the method of claim 40.

54. A method of particle analysis using the apparatus according to claim 1, the method comprising the sequential steps of:
  i) introducing a powder sample into the receptacle (3);
  ii) oscillating the oscillatory assembly in order to cause particles of the powder sample that are smaller than the opening of the receptacle to exit the receptacle (S105, S205);
  iii) allowing the oscillations of the oscillatory assembly to cease;
  iv) measuring a signal produced by the sensor means while the oscillatory assembly is stationary.

55. A method for separating a powder sample into different size fractions using the apparatus of claim 1, the method comprising the steps of:
  varying the size of the opening to a first size;
  introducing a powder sample into the receptacle;
  inducing oscillations of the oscillatory assembly (S105, S205);
  collecting a first size fraction of particles of the powder sample discharged from the receptacle;
  varying the size of the opening to a second size (S120); and
  collecting a second size fraction of particles of the powder sample discharged from the receptacle.

56. A particle size fraction produced by the method of claim 55.

* * * * *